(12) United States Patent
Liu

(10) Patent No.: US 11,497,936 B2
(45) Date of Patent: Nov. 15, 2022

(54) MULTI-LEAF COLLIMATOR

(71) Applicant: SHANGHAI UNITED IMAGING HEALTHCARE CO., LTD., Shanghai (CN)

(72) Inventor: Yanfang Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 17/131,808

(22) Filed: Dec. 23, 2020

(65) Prior Publication Data

US 2021/0106845 A1 Apr. 15, 2021

Related U.S. Application Data

(63) Continuation of application No. PCT/CN2019/095791, filed on Jul. 12, 2019.

(51) Int. Cl.
*A61N 5/10* (2006.01)
*G21K 1/04* (2006.01)
(Continued)

(52) U.S. Cl.
CPC .............. *A61N 5/1045* (2013.01); *A61B 6/06* (2013.01); *A61B 6/547* (2013.01); *A61N 5/1048* (2013.01);
(Continued)

(58) Field of Classification Search
CPC .. A61N 5/1036; A61N 5/1042; A61N 5/1045; A61N 5/1047; A61N 5/1048; A61N 5/1064; A61N 5/0165; A61N 5/1067; A61N 2005/1092; A61N 2005/1095; A61B 5/70; A61B 5/706; A61B 6/06; A61B 6/08; A61B 6/44; A61B 6/4476; A61B 6/54; A61B 6/547; A61B 6/548; A61B 6/58;
(Continued)

(56) References Cited

U.S. PATENT DOCUMENTS 4,794,629 A * 12/1988 Pastyr .................. A61N 5/1042
378/146
10,892,064 B2 1/2021 Stahl et al.
(Continued)

FOREIGN PATENT DOCUMENTS

CN 101890208 A 11/2010
CN 101000808 B 12/2010
(Continued)

OTHER PUBLICATIONS

International Search Report in PCT/CN2019/095791 dated Apr. 13, 2020, 5 pages.
(Continued)

*Primary Examiner* — Anastasia Midkiff
(74) *Attorney, Agent, or Firm* — Metis IP LLC

(57) ABSTRACT

The present disclosure relates a multi-leaf collimator. The multi-leaf collimator may include a plurality of leaves. At least two leaves of the plurality of leaves may be movable parallel to each another. For each leaf of at least some of the plurality of leaves, at least one portion of the leaf may have thicknesses varying along a longitudinal direction of the each leaf. The each leaf may have a first end and a second end along the longitudinal direction of the each leaf.

19 Claims, 12 Drawing Sheets

(51) Int. Cl.
*A61B 6/06* (2006.01)
*A61B 6/00* (2006.01)
*A61B 90/00* (2016.01)
*A61B 34/20* (2016.01)
*H01J 37/09* (2006.01)

(52) U.S. Cl.
CPC ...... *G21K 1/046* (2013.01); *A61B 2034/2055* (2016.02); *A61B 2090/0811* (2016.02); *A61B 2560/0266* (2013.01); *A61B 2562/0257* (2013.01); *A61N 5/1047* (2013.01); *A61N 5/1081* (2013.01); *H01J 37/09* (2013.01); *H01J 2237/0455* (2013.01); *H01J 2237/1504* (2013.01)

(58) Field of Classification Search
CPC ......... A61B 6/586; A61B 34/10; A61B 34/20; A61B 90/10; A61B 2034/107; A61B 2034/2046; A61B 2034/2055; A61B 2090/0807; A61B 2090/0811; A61B 2560/02; A61B 2560/0266; A61B 2560/04; A61B 2562/02; A61B 2562/0257; G21K 1/02; G21K 1/04; G21K 1/046; G21K 5/04; H01J 37/09; H01J 37/147; H01J 2237/04; H01J 2237/045; H01J 2237/0453; H01J 2237/0455; H01J 2237/0456; H01J 2237/0458; H01J 2237/083; H01J 2237/0835; H01J 2237/15; H01J 2237/1502; H01J 2237/1504
See application file for complete search history.

(56) References Cited

U.S. PATENT DOCUMENTS

| | | | |
|---|---|---|---|
| 2006/0193441 A1* | 8/2006 | Cadman | A61N 5/1042 378/153 |
| 2008/0205599 A1* | 8/2008 | Hashimoto | G21K 1/04 378/148 |
| 2010/0260319 A1* | 10/2010 | Ein-Gal | A61N 5/1042 378/65 |
| 2014/0239204 A1 | 8/2014 | Orton et al. | |
| 2015/0273239 A1* | 10/2015 | Hsu | A61N 5/1045 378/150 |
| 2018/0200540 A1* | 7/2018 | Flynn | A61N 5/1001 |
| 2019/0175944 A1 | 6/2019 | Towe et al. | |

FOREIGN PATENT DOCUMENTS

| | | |
|---|---|---|
| CN | 102755696 A | 10/2012 |
| CN | 103272338 A | 9/2013 |
| CN | 103301580 A | 9/2013 |
| CN | 104474639 A | 4/2015 |
| CN | 205145403 U | 4/2016 |

OTHER PUBLICATIONS

Written Opinion in PCT/CN2019/095791 dated Apr. 13, 2020, 5 pages.
First Office Action in Chinese Application No. 201980043457.1 dated Jun. 2, 2022, 17 pages.

* cited by examiner

MULTI-LEAF COLLIMATOR

CROSS-REFERENCE TO RELATED APPLICATIONS

This application is a continuation of International Patent Application No. PCT/CN2019/095791, filed on Jul. 12, 2019, the contents of which are hereby incorporated by reference.

TECHNICAL FIELD

The present disclosure generally relates to radiotherapy, and more specifically relates to a multi-leaf collimator (MLC), systems and methods for determining a position of each leaf of the MLC.

BACKGROUND

Radiotherapy has been widely employed in cancer therapy by directing ionizing radiation towards a tumor. Considerations of radiotherapy include that the tumor receives sufficient radiation, while the damage to an organ at risk (OAR) is minimized as much as possible during the radiotherapy. Multi-leaf collimator (MLC) is commonly used in radiotherapy to implement the precise delivery of radiation to the tumor. For instance, by moving each leaf of the MLC to multiple desired positions, various radiation fields may be formed, which may conform to the shape(s) of the tumor. That is, in order to ensure the radiation source delivers a correctly shaped dose, the position of each leaf should be accurately determined. Thus, it is desirable to provide a system and method for determining a position of each leaf of the MLC.

SUMMARY

In one aspect of the present disclosure, a multi-leaf collimator is provided. The multi-leaf collimator may include a plurality of leaves. At least two leaves of the plurality of leaves may be movable parallel to each another. At least one portion of each leaf of at least some of the plurality of leaves may have thicknesses varying along a longitudinal direction of the each leaf. The each leaf may have a first end and a second end along the longitudinal direction of the each leaf.

In some embodiments, at least one of a lower edge or an upper edge of the at least one portion of the each leaf may be unparallel to the longitudinal direction such that different locations of the at least one portion of the each leaf have different thicknesses along the longitudinal direction.

In some embodiments, the thicknesses of the at least one portion of the each leaf may vary linearly along the longitudinal direction of the each leaf.

In some embodiments, the thicknesses of the at least one portion of the each leaf may vary non-linearly along the longitudinal direction of the each leaf.

In some embodiments, the first end of the each leaf may have a maximum thickness and the second end of the each leaf may have a minimum thickness within the each leaf.

In some embodiments, the multi-leaf collimator may also include a measurement device mounted to a fixed position of a radiation system and configured to determine a height of the each leaf at a specific location in the longitudinal direction. The height of the each leaf at the specific location may be used to determine a position of the first end or the second end of the each leaf.

In some embodiments, the height of the each leaf at the specific location may refer to the thickness of the each leaf at the specific location.

In some embodiments, the height of the each leaf at the specific location may relate to a distance between the specific location on a lower edge or an upper edge of the each leaf and a reference plane.

In some embodiments, the multi-leaf collimator may also include a second measurement device mounted to a second fixed position of the radiation system and configured to determine a second height of the each leaf at a second specific location in the longitudinal direction. The height of the each leaf at the specific location and the second height of the each leaf at the second specific location may be used to determine the position of the first end or the second end of the each leaf.

In some embodiments, the measurement device may include one or more measurement components configured to determine a height of the each leaf at the specific location in the longitudinal direction.

In some embodiments, the measurement device may include a plurality of measurement components. Each of the plurality of measurement components may be configured to determine a height of one of the at least some of the plurality of leaves at the specific location in the longitudinal direction.

In another aspect of the present disclosure, a system is provided. The system may include at least one storage device, and at least one processor in communication with the at least one storage device. The at least one storage device may include a set of instructions for determining a position of a leaf in a multi-leaf collimator. When executing the set of instructions, the at least one processor may be configured to cause the system to perform operations including obtaining a length-height correspondence of the leaf, wherein at least one portion of the leaf has thicknesses varying along a longitudinal direction of the leaf, the leaf having a first end and a second end along the longitudinal direction of the leaf; determining a height of the leaf at a specific location using a measurement device; and determining a position of the first end of the leaf based on the height of the leaf at the specific location and the length-height correspondence of the leaf.

In some embodiments, the at least one processor may be configured to cause the system to perform additional operations including determining a second height of the leaf at a second specific location using a second measurement device; and determining a second position of the first end of the leaf based on the second height of the leaf at the second specific location and the length-height correspondence of the leaf.

In some embodiments, the at least one processor may be configured to cause the system to perform additional operations including determining a difference between the position and the second position of the first end of the leaf; and in response to a determination that the difference between the position and the second position of the first end of the leaf is less than a threshold, determining an average of the position and the second position as a final position of the first end.

In some embodiments, the at least one processor may be configured to cause the system to perform additional operations including in response to a determination that the difference between the position and the second position of the first end of the leaf exceeds the threshold, re-determining the position of the first end using the measurement device and/or the second position of the first end using the second measurement device.

In some embodiments, at least one of a lower edge or an upper edge of the at least one portion of the leaf may be unparallel to the longitudinal direction such that different locations of the at least one portion of the leaf have different thicknesses along the longitudinal direction.

In some embodiments, the thicknesses of the at least one portion of the leaf may vary linearly or non-linearly along the longitudinal direction of the leaf.

In some embodiments, the length-height correspondence of the leaf may relate to the thickness of the leaf at a location within the at least one portion of the leaf.

In some embodiments, the length-height correspondence of the leaf may relate to a distance between a location on the lower edge or the upper edge within the at least one portion of the leaf and a reference plane.

In yet another aspect of the present disclosure, a method is provided. The method may be implemented on a computing device having at least one processor, at least one computer-readable storage medium, and a communication platform connected to a network. The method may include obtaining a length-height correspondence of a leaf, wherein at least one portion of the leaf has thicknesses varying along a longitudinal direction of the leaf, the leaf having a first end and a second end along the longitudinal direction of the leaf; determining a height of the leaf at a specific location using a measurement device; and determining a position of the first end of the leaf based on the height of the leaf at the specific location and the length-height correspondence of the leaf.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Figure 2:
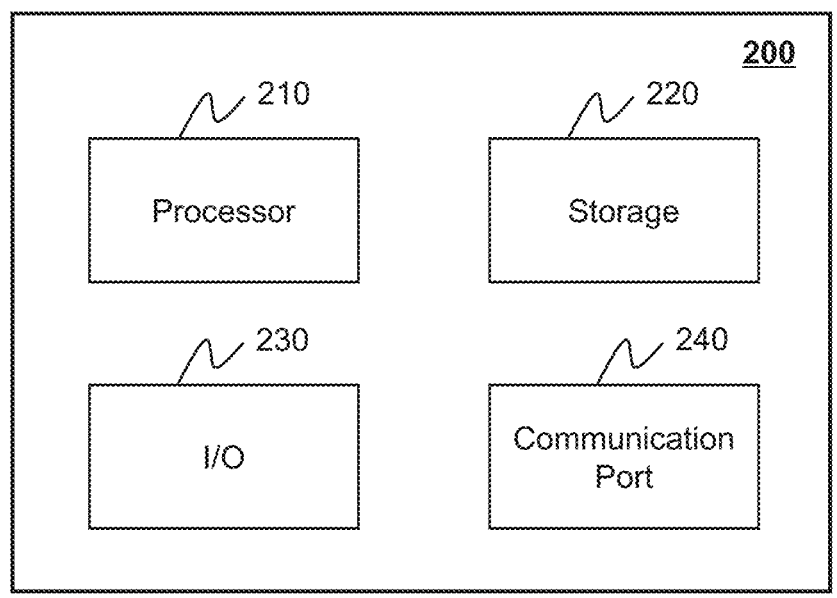
FIG. 2 is a schematic diagram illustrating exemplary hardware and/or software components of a computing device on which the processing device may be implemented according to some embodiments of the present disclosure.

Generally, the word "module," "unit," or "block," as used herein, unless otherwise defined, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/ blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure relates to a multi-leaf collimator. The multi-leaf collimator may include a plurality of leaves. At least two leaves of the plurality of leaves may be movable parallel to each another. For each leaf of at least some of the plurality of leaves, at least a portion of the leaf may have thicknesses varying along a longitudinal direction of the leaf, and accordingly the lower edge or the upper edge of the at least one portion of the leaf may be unparallel to the longitudinal direction.

Figure 1:
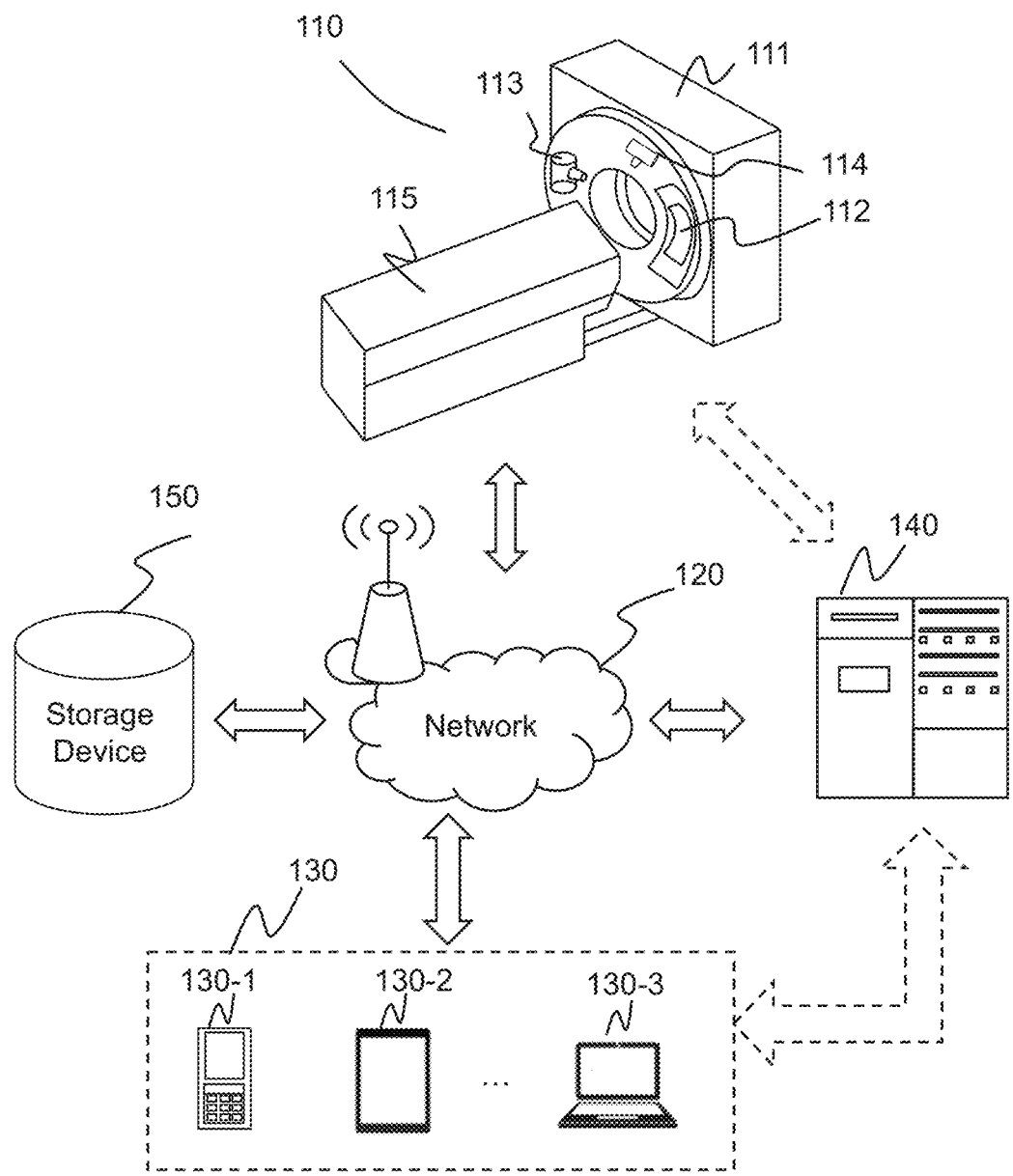
FIG. 1 is a schematic diagram illustrating an exemplary radiation system according to some embodiments of the present disclosure.

FIG. 1 is a schematic diagram illustrating an exemplary radiation system according to some embodiments of the present disclosure. The radiation system 100 may include a radiation delivery device 110, a network 120, one or more terminals 130, a processing device 140, and a storage device 150. The components of the radiation system 100 may be connected in various ways. Merely by way of example, the radiation delivery device 110 may be connected to the processing device 140 through the network 120. As another example, the radiation delivery device 110 may be connected to the processing device 140 directly as indicated by the bi-directional arrow in dotted lines linking the radiation delivery device 110 and the processing device 140. As a further example, the storage device 150 may be connected to the processing device 140 directly or through the network 120. As still a further example, the terminal 130 may be connected to the processing device 140 directly (as indicated by the bi-directional arrow in dotted lines linking the terminal 130 and the processing device 140) or through the network 120.

In some embodiments, the radiation delivery device 110 may simultaneously perform imaging and treatment on an object. Merely by way of example, the radiation delivery device 110 may include an imaging assembly, a treatment radiation source (e.g., the first radiation source 114), a gantry 111, and a table 115. The imaging assembly may include a conventional CT, a cone beam CT (CBCT), a helical CT, a multi-slice CT, a PET-CT, or the like, or any combination thereof. The imaging assembly may be configured to generate one or more images before, during or after radiotherapy. As shown in FIG. 1, the imaging assembly may include an imaging radiation source (e.g., the second radiation source 113) and a radiation detector 112 opposite to the second radiation source 113. In some embodiments, the gantry 111 may include a rotary ring (not shown in FIG. 1). The rotary ring may be configured to accommodate the second radiation source 113, the radiation detector 112, and the first radiation source 114. Alternatively, the gantry 111 may include two rotary rings (not shown in FIG. 1). One rotary ring may be configured to accommodate the imaging assembly (i.e., the second radiation source 113 and the radiation detector 112), and the other rotary ring may be configured to accommodate the first radiation source 114. In some embodiments, the first radiation source 114 may emit a first beam toward a first region (e.g., a tumor) of an object that is placed on the table 115. The second radiation source 113 may emit a second beam toward a second region (e.g., an imaging region) of the object. In some embodiments, the intensity of the first beam may be different from the intensity of the second beam. For example, the energy of the first beam may be several megavolts (MV), this energy being greater than that of the second beam, which may be several kilovolts (kV). The object may be a biological object (e.g., a patient, an animal) or a non-biological object. In the present disclosure, "object" and "subject" are used interchangeably. The radiation detector 112 may be configured to detect radiation emitted from the second radiation source 113. It should be noted that the above descriptions of the radiation delivery device 110 are merely provided for the purposes of illustration, and not intended to limit the scope of the present disclosure. In some embodiments, the imaging assembly in the radiation delivery device 110 may be omitted, and the radiation delivery device 110 may include only one radiation source (e.g., the first radiation source 114) for delivering radiation for radiotherapy or imaging.

In some embodiments, the radiation delivery device 110 may further include one or more MLCs (not shown in FIG. 1). The MLC(s) may be configured to collimate the radiation beam(s) of the radiation delivery device 110 and/or define the beam shape(s) thereof to form one or more radiation fields. An MLC may include multiple leaves. In some embodiments, the first radiation source 114 may include or be associated with an MLC. More descriptions of the MLC may be found elsewhere in the present disclosure (e.g., FIGS. 4A and 5, and the descriptions thereof).

The network 120 may facilitate the exchange of information and/or data. In some embodiments, one or more components of the radiation system 100 (e.g., the radiation delivery device 110, the terminal 130, the processing device 140, or the storage device 150) may send information and/or data to another component(s) in the radiation system 100 via the network 120. For example, the processing device 140 may obtain, via the network 120, a length-height correspondence of each leaf from the storage device 150. In some embodiments, the network 120 may be any type of wired or wireless network, or combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired or wireless network access points such as base stations and/or internet exchange points through which one or more components of the radiation system 100 may be connected to the network 120 to exchange data and/or information.

The terminal 130 include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal 130 may remotely operate the radiation delivery device 110. In some embodiments, the terminal 130 may operate the radiation delivery device 110 via a wireless connection. In some embodiments, the terminal 130 may receive information and/or instructions inputted by a user, and send the received information and/or instructions to the radiation delivery device 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

In some embodiments, the processing device 140 may process data obtained from the radiation delivery device 110, the terminal 130, or the storage device 150. For example, the processing device 140 may determine a position of a first end of each leaf of an MLC. The processing device 140 may be a central processing unit (CPU), a digital signal processor (DSP), a system on a chip (SoC), a microcontroller unit (MCU), or the like, or any combination thereof. In some embodiments, the processing device 140 may be a single server or a server group. The server group may be centralized or distributed. In some embodiments, the processing device 140 may be local or remote. For example, the processing device 140 may access information and/or data stored in the radiation delivery device 110, the terminal 130, and/or the storage device 150 via the network 120. As another example, the processing device 140 may be directly connected to the radiation delivery device 110 (as illustrated by the dashed bidirectional arrow linking the radiation delivery device 110 and the processing device 140 in FIG. 1), the terminal 130 (as illustrated by the dashed bidirectional arrow linking the terminal 130 and the processing device 140 in FIG. 1), and/or the storage device 150, to access information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the radiation system 100 (e.g., the terminal 130, the processing device 140). One or more components of the radiation system 100 may access the data or instructions stored in the storage device 150 via the network 120. In some embodiments, the storage device 150 may be directly connected to or communicate with one or more components of the radiation system 100 (e.g., the terminal 130, the processing device 140). In some embodiments, the storage device 150 may be part of the processing device 140.

FIG. 2 is a schematic diagram illustrating exemplary hardware and/or software components of a computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and, when executing the instructions, cause the processing device 140 to perform functions of the processing device 140 in accordance with techniques described herein. The computer instructions may include, for example, routines, programs, objects, components, signals, data structures, procedures, modules, and functions, which perform particular functions described herein. In some embodiments, the processor 210 may process data and/or images obtained from the radiation delivery device 110, the terminal 130, the storage device 150, and/or any other component of the radiation system 100. For example, the processor 210 may determine a height of each leaf at a specific location using a measurement device. As another example, the processor 210 may determine a position of a first end of each leaf based on the height of the corresponding leaf at the specific location and a length-height correspondence of the corresponding leaf. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the radiation delivery device 110, the terminal 130, the storage device 150, or any other component of the radiation system 100. In some embodiments, the storage 220 may include amass storage device, removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure.

The I/O 230 may input or output signals, data, and/or information. In some embodiments, the I/O 230 may enable a user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the radiation delivery device 110, the terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMAX, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
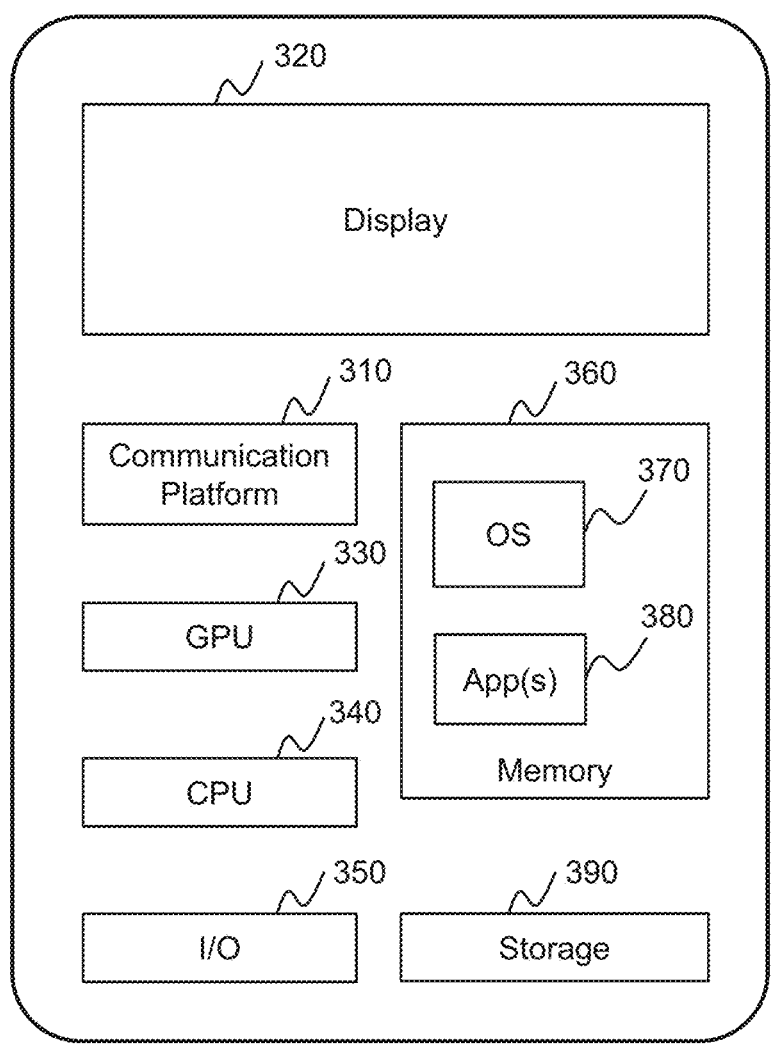
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the radiation system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to determine a position of each leaf of a multi-leaf collimator as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4A:
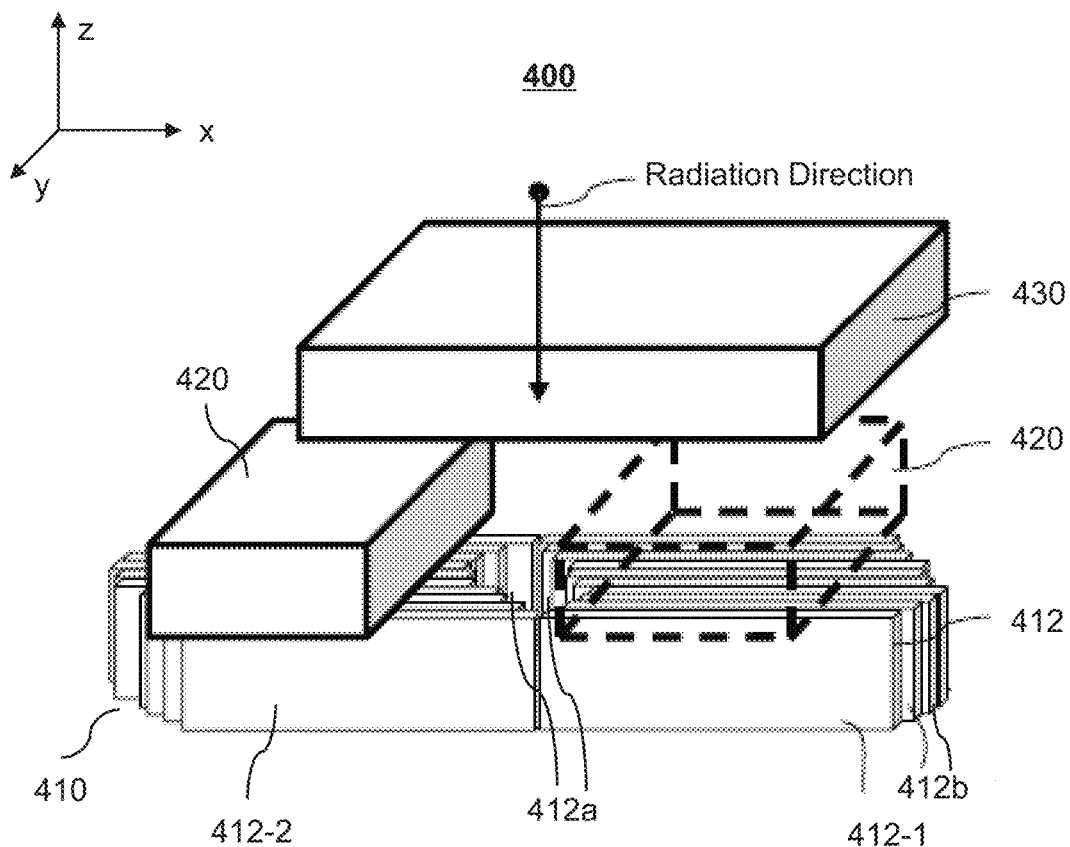
FIG. 4A is a schematic diagram illustrating an exemplary collimating assembly according to some embodiments of the present disclosure.

FIG. 4A is a schematic diagram illustrating an exemplary collimating assembly 400 according to some embodiments of the present disclosure. As shown in FIG. 4A, the collimating assembly 400 may include an MLC 410 including a plurality of leaves 412. Preferably, the MLC 410 may include 64 leaves. However, it shall be understood that the number or count of the leaves in the MLC 410 may vary. For example, the number or count of the leaves in the MLC 410 may be 12, 24, 32, 48, 80, 100, 128, etc. It should be noted that the collimating assembly 400 may include two or more MLCs (not shown in FIG. 4A). The two or more MLCs may be the same. Alternatively, at least two of the MLCs may be different. For example, a first MLC may include a first number or count of leaves, and a second MLC may include a second number or count of leaves. As another example, the shapes of leaves in the first MLC may be different from the shapes of the leaves in the second MLC. In some embodiments, if there are two MLCs, the two MLCs may be arranged perpendicular to each other. If there are three MLCs, the three MLCs may be arranged at intervals of 60°.

At least two leaves of the plurality of leaves may be movable parallel to each another (e.g., being movable along the x-direction). In some embodiments, all leaves of the MLC 410 may be configured to move parallel to each other independently. In some embodiments, the leaves of the MLC 410 may be arranged in groups, in which each group includes at least one leaf; leaves within the same group may be arranged on one side of the MLC 410 (e.g., one or more leaves 412-1 that are arranged on the right side of the MLC 410 as indicated in FIG. 4A) and configured to move parallel to each other; leaves of different groups may be arranged to face each other (e.g., one or more leaves 412-1 within a first group and one or more leaves 412-2 within a second group) and configured to move parallel to each other or not. In some embodiments, all leaves of the MLC 410 may be configured to move synchronously or not. For example, leaves within the same group may be configured to move synchronously, and leaves of different groups may be configured to move synchronously or asynchronously.

Each leaf 412 may include a first end (also referred to as a front end) and a second end (also referred to as a rear end) located at the ends of a leaf along the longitudinal direction of the leaf (e.g., along the x-direction). As illustrated in FIG. 4A, the front end 412a of a leaf (e.g., leaf 412-1) may refer to the end of the leaf that faces an end of another leaf (e.g., leaf 412-2). The rear end 412b may refer to the other end of the leaf (e.g., leaf 412-1). In order to shield a portion of radiation beams emitted by the radiation source (e.g., the first radiation source 114), the plurality of leaves 412 may be made of radiation-impermeable materials (e.g., tungsten). The collimating assembly 400 may also include one or more jaws moving along the x-direction (also referred to as parallel jaws 420) and one or more jaws moving along the y-direction (also referred to as perpendicular jaws 430). In some embodiments, there may be two parallel jaws 420 (as illustrated by the parallel jaw 420 in solid lines and the parallel jaw 420 in dashed lines in FIG. 4A, the parallel jaw 420 in solid lines being same as or different from the parallel jaw 420 in dashed lines) and two perpendicular jaws 430 (only one shown in FIG. 4A). It should be noted that, the jaws (the parallel jaws 420 and/or the perpendicular jaws 430) may be placed below the MLC 410 (not shown in FIG. 4A).

Figure 4B:
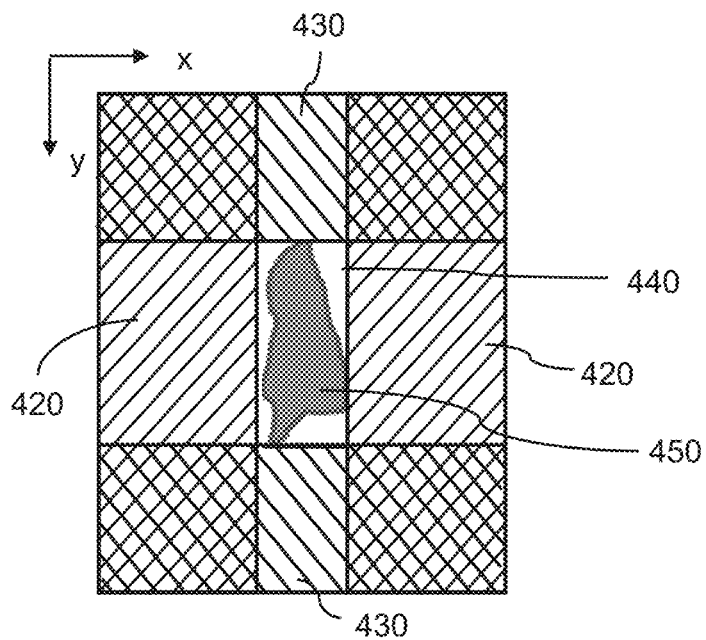
FIG. 4B is a schematic diagram illustrating an exemplary treatment region formed by jaws and an MLC according to some embodiments of the present disclosure.

The parallel jaws 420 and/or the perpendicular jaws 430 may be made of radiation-impermeable materials (e.g., tungsten), and used to shield a portion of radiation beams emitted by the radiation source (e.g., the first radiation source 114). As shown in FIG. 4A, radiation beams may travel along the z-direction, and pass through a region shaped by jaws (e.g., the parallel jaws 420, the perpendicular jaws 430) and the MLC 410 (or two or more MLCs) to reach a target object (e.g., a tumor). In some embodiments, the parallel jaws 420 and/or the perpendicular jaws 430 may cooperate or coordinate with the MLC 410 to define a desired aperture (also referred to as a radiation field) that matches (or approximately matches) a desired treatment region (e.g., a treatment region 450 as shown in FIG. 4B). For example, the parallel jaws 420 and the perpendicular jaws 430 may be moved to define a range of a radiation field. For instance, the parallel jaws 420 and the perpendicular jaws 430 may define a rectangular region of radiation field (e.g., a rectangular region 440 as shown in FIG. 4B). The plurality of leaves 412 may be moved to further define a desired aperture. The radiation beams may reach the desired treatment region (e.g., the treatment region 450) via the aperture.

Generally, in order to effectively block radiation beams, the thickness of the leaves 412 (which is along the z-direction) may need to satisfy a criterion. For example, the thickness of the leaves 412 may need to be equal to or greater than a threshold (e.g., 4.5 cm, 5 cm, 7.5 cm, etc.). As described in connection with FIG. 4B, for each leaf 412, a portion of the leaf 412 that is away from the front end of the leaf 412 (e.g., a portion out of the rectangular region 440) may be shielded by the jaws, thus being protected from the radiation beams. Therefore, the thickness of the portion of each leaf 412 that is away from the front end of the leaf 412 (a portion out of the rectangular region 440) may be equal to or less than the threshold, and the total weight of the MLC 410 may be reduced, which may improve the stability of the MLC 410, extend MLC's service life, and reduce deformation of the leaves 412 of the MLC 410.

Figure 5:
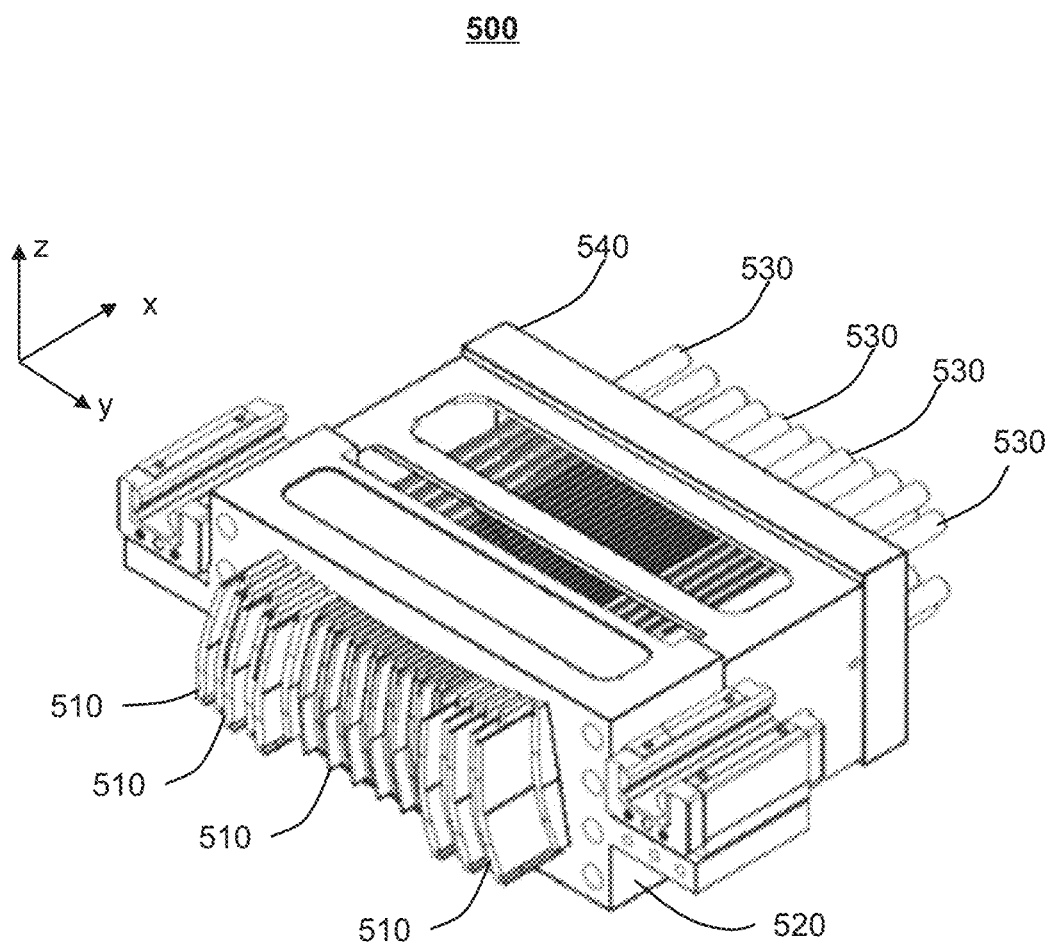
FIG. 5 is a schematic diagram illustrating an exemplary MLC according to some embodiments of the present disclosure.

FIG. 5 is a schematic diagram illustrating an exemplary MLC 500 according to some embodiments of the present disclosure. As shown in FIG. 5, the MLC 500 may include a plurality of leaves 510, a guide rail box 520, a plurality of drive mechanisms (e.g., a plurality of motors) 530, and a motor base 540. The guide rail box 520 may include a plurality of guide rails. Each guide rail of the plurality of guide rails may be configured to guide a movement of a leaf of the plurality of leaves 510. The plurality of drive mechanisms 530 may be supported by and/or accommodated within the motor base 540. The plurality of drive mechanisms 530 may be configured to actuate the plurality of leaves 510 to move along the plurality of guide rails. The plurality of leaves 510 may be configured to shield a portion of radiation beams emitted by a radiation source (e.g., the first radiation source 114).

In some embodiments, at least some of the plurality of leaves 510 may be actuated or moved simultaneously. By simultaneously actuating and/or moving at least some of the plurality of leaves 510, an aperture (also referred to as a radiation field) may be formed. A portion of radiation beams emitted from the radiation source (e.g., the first radiation source 114) may pass through the aperture, and further be delivered to a treatment region (e.g., a tumor). The other portion of radiation beams may be blocked by the leaves 510 of the MLC 500 and/or the parallel jaws 420 and perpendicular jaws 430. In some embodiments, the plurality of drive mechanisms 530 may facilitate the movement of the plurality of leaves 510 such that the MLC 500 can define different apertures (e.g., change a first aperture shape to a second aperture shape). For example, a leaf 510 may be actuated, by a corresponding drive mechanism 530, to move from a first position (e.g., the current position) to a second position (e.g., a desired position). In some embodiments, the MLC 500 may be a binary MLC, each leaf of which is movable between two positions (i.e., closed and open positions); or may be an MLC, each leaf of which is movable between more than two positions. Descriptions regarding an MLC whose leaves are movable between a plurality of positions may be found in, e.g., American application Ser. No. 16/210,124, entitled "MULTI-LEAF COLLIMATOR," filed on Dec. 5, 2018, which is incorporated by reference.

In some embodiments, the parallel jaws 420 and/or the perpendicular jaws 430 are placed above/or below the MLC 500, and a portion of a leaf 510 may be shielded by the parallel jaws 420 and/or the perpendicular jaws 430. A portion of radiation beams may be blocked by the parallel jaws 420 and/or the perpendicular jaws 430, and thus, the portion of a leaf 510 shielded by the parallel jaws 420 and/or the perpendicular jaws 430 may be shielded from radiation beams. In some embodiments, a portion of a leaf 510 near a second end (e.g., the rear end 412-b shown in FIG. 4A) may be shielded by the parallel jaws 420 and/or the perpendicular jaws 430, and thus the thickness of the portion of the leaf 510 near the second end (e.g., the second end 412-b) may be smaller than the other portion of the leaf 510 (the parallel jaws 420 and/or the perpendicular jaws 430 do not shield the other portion of the leaf 510). It should be understood that the above descriptions are merely an example, and are not intended to limit the scope of the present disclosure. In some embodiments, the portion of each leaf 510 near the second end may have a relatively greater thickness than the other portion of the each leaf 510, or have the same thickness as the other portion of the each leaf 510.

Generally, when other conditions (e.g., the size of beam spots, the structure of the leaves, the arrangement of the leaves, etc.) are determined, the penumbra may relate to the thickness (which is along the z-direction) of a front end of a leaf 510 of the MLC 500. For example, the greater the thickness of the front end of a leaf 510 is, the smaller the penumbra is. In some embodiments, when other conditions (e.g., the size of beam spots, the structure of the leaves, the arrangement of the leaves, etc.) are determined, the leakage of radiation emitted by the radiation source (e.g., the first radiation source 114) may relate to the thickness of a portion of a leaf 510 irradiated by the radiation source. For example, the greater the thickness of the portion of a leaf 510 is, the smaller the leakage of radiation is. In some embodiments of the present disclosure, a leaf 510 of the MLC 500 may have a first end (e.g., the front end 412a shown in FIG. 4A) and a second end (e.g., the rear end 412b shown in FIG. 4A) along the longitudinal direction of the leaf 510. In some embodiments, the first end of a leaf 510 may have the maximum thickness and the second end of the leaf 510 may have the minimum thickness within the leaf. That is, a leaf 510 of the MLC 500 may have thicknesses varying along the longitudinal direction of the leaf 510 (i.e., along the x-direction). Compared with a reference MLC whose leaves have the same thickness along the longitudinal direction of the leaf, if the weight of the reference MLC and the MLC 500 are the same, the front end of a leaf 510 of the MLC 500 may have a larger thickness than that of the reference MLC, thus facilitating to reduce the penumbra. Besides, the portion of a leaf 510 of the MLC 500 irradiated by the radiation source (e.g., the first radiation source 114) may have a larger thickness than that of the reference MLC, thus facilitating to reduce the leakage of radiation. Alternatively, when the penumbra and/or the leakage of radiation of the reference MLC and the MLC 500 are the same, the MLC 500 may have a smaller weight than the reference MLC. In other words, the MLC 500 may be configured to decrease penumbra and/or decrease leakage of radiation.

In some embodiments, at least one portion of a leaf 510 may have thicknesses varing along the longitudinal direction of the leaf 510. In some embodiments, at least one of a lower edge or an upper edge of the at least one portion of the leaf 510 may be unparallel to the longitudinal direction (i.e., the x-direction) such that different locations of the at least one portion of the leaf 510 have different thicknesses along the longitudinal direction. The upper edge and/or the lower edge of a leaf may be a surface of the leaf that is perpendicular to radiation beams emitted by the first radiation source 114. The upper edge of the leaf 510 may be closer to the first radiation source 114 than the lower edge of the leaf 510. Radiation beams from the first radiation source 114 may enter the MLC 500 from the upper edges of the leaves 510 and travel toward the lower edges of the leaves 510.

Figure 6A:
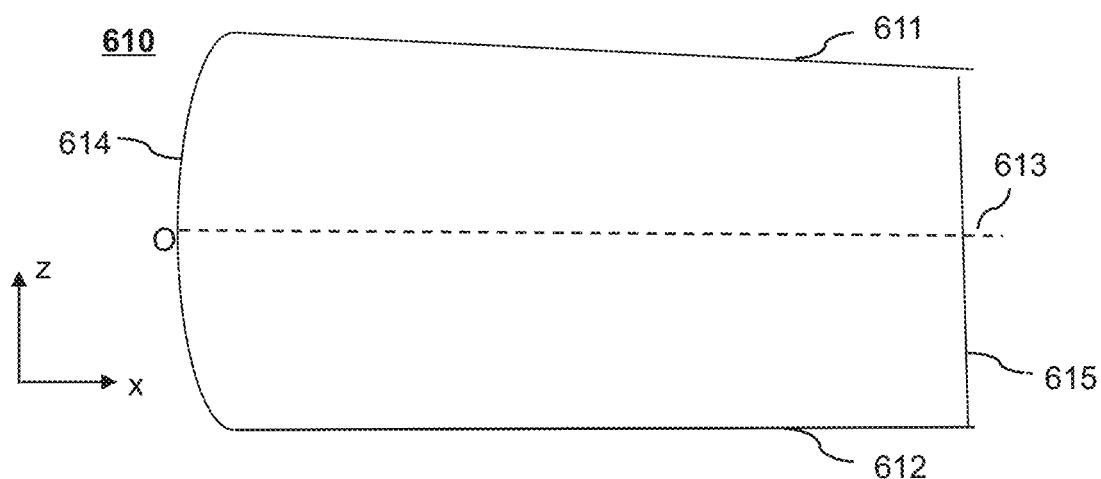
FIGS. 6A through 6I illustrate exemplary leaves according to some embodiments of the present disclosure.

In some embodiments, the leaf 510 may have thicknesses varying along the longitudinal direction of at least a portion of the leaf 510. In some embodiments, an upper edge of the leaf 510 may be unparallel to the longitudinal direction of the leaf 510. Merely by way of example, FIG. 6A illustrates an exemplary leaf 610. As shown in FIG. 6A, the lower edge 612 of the leaf 610 is parallel to the longitudinal direction of the leaf 610 (i.e., the x-direction), and the upper edge 611 of the leaf 610 is unparallel to the longitudinal direction of the leaf 610 (i.e., the x-direction). Specifically, the upper edge 611 may tilt toward a center axis 613 of the leaf 610 from the front end 614 to the rear end 615. In other words, distances between locations (or points) on the upper edge 611 and the center axis 613 of the leaf 610 may gradually decrease from the front end 614 to the rear end 615. The thicknesses of the leaf 610 may gradually decrease along the longitudinal direction of the leaf 610 from the front end 614 to the rear end 615. The center axis 613 may refer to a line parallel to the x-direction that passes through a center point O of the front end 614.

Figure 6B:
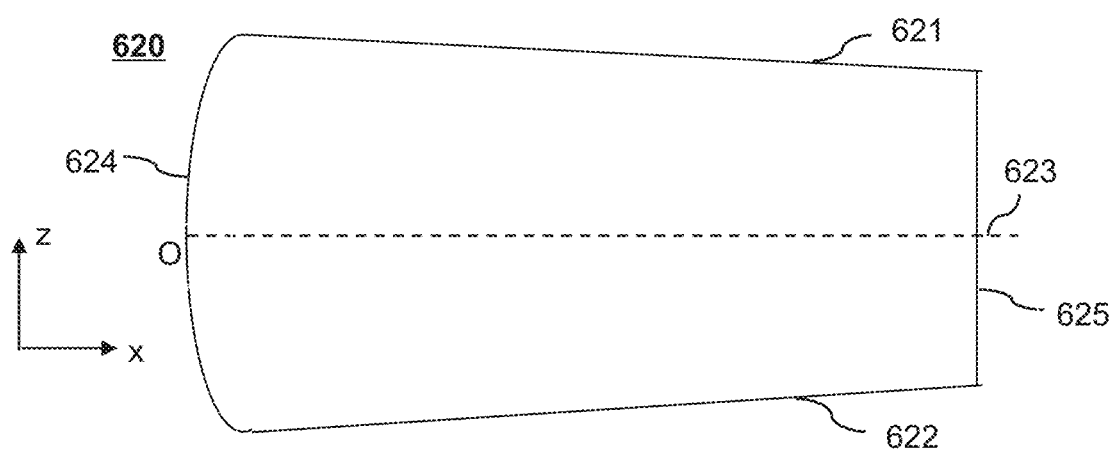
Figure 6C:
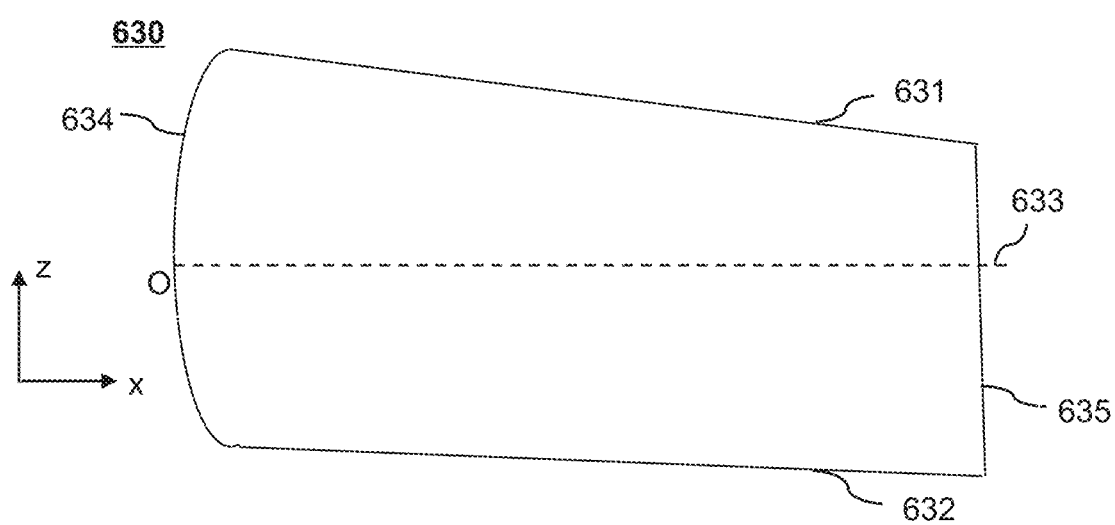

In some embodiments, both an upper edge and a lower edge of the leaf 510 may be unparallel to the longitudinal direction of the leaf 510. For illustration purposes, FIG. 6B illustrates an exemplary leaf 620 and FIG. 6C illustrates an exemplary leaf 630. As shown in FIG. 6B, the upper edge 621 and the lower edge 622 of the leaf 620 may be unparallel to the longitudinal direction of the leaf 620. Specifically, the upper edge 621 and the lower edge 622 of the leaf 620 may both gradually tilt toward a center axis 623 of the leaf 620 from the front end 624 to the rear end 625. In other word, distances between locations (or points) on the upper edge 621 and the center axis 623 of the leaf 620 may gradually decrease from the front end 614 to the rear end 615, and distances between locations (or points) on the lower edge 622 of the leaf 620 and the center axis 623 of the leaf 620 may also gradually decrease from the front end 624 to the rear end 625. The thicknesses of the leaf 620 may gradually decrease along the longitudinal direction of the leaf 620 (i.e., the x-direction) from the front end 624 to the rear end 625.

As shown in FIG. 6C, the upper edge 631 and the lower edge 632 of the leaf 630 may be unparallel to the longitudinal direction of the leaf 630. Specifically, the upper edge 631 of the leaf 630 may gradually tilt toward a center axis 633 of the leaf 630 from the front end 634 to the rear end 635, while the lower edge 632 of the leaf 630 may gradually tilt away from the center axis 633 of the leaf 630 from the front end 634 to the rear end 635. In other words, distances between locations (or points) on the upper edge 631 of the leaf 630 and the center axis 623 of the leaf 630 may gradually decrease from the front end 634 to the rear end 635, while distances between locations (or points) on the lower edge 632 of the leaf 630 and a center axis 623 of the leaf 630 may gradually increase from the front end 634 to the rear end 635. The thicknesses of the leaf 630 may gradually decrease along the longitudinal direction of the leaf 630 (i.e., the x-direction) from the front end 634 to the rear end 635.

Figure 6D:
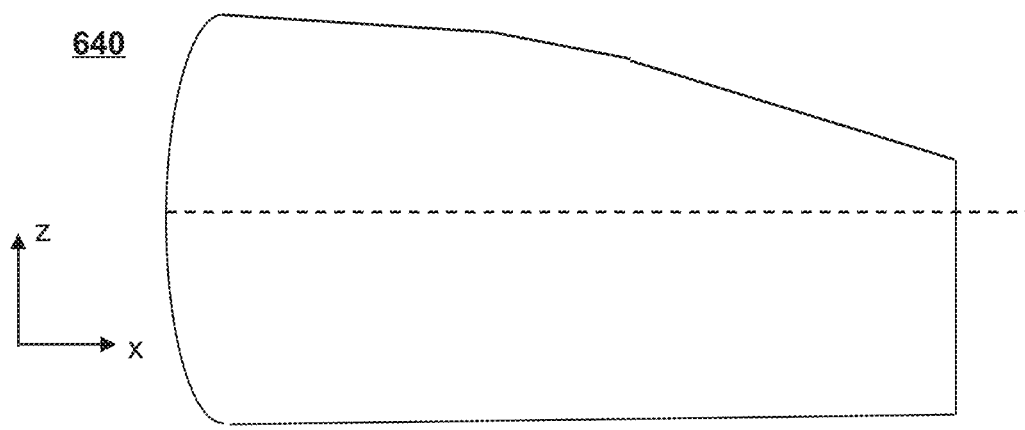
Figure 6E:
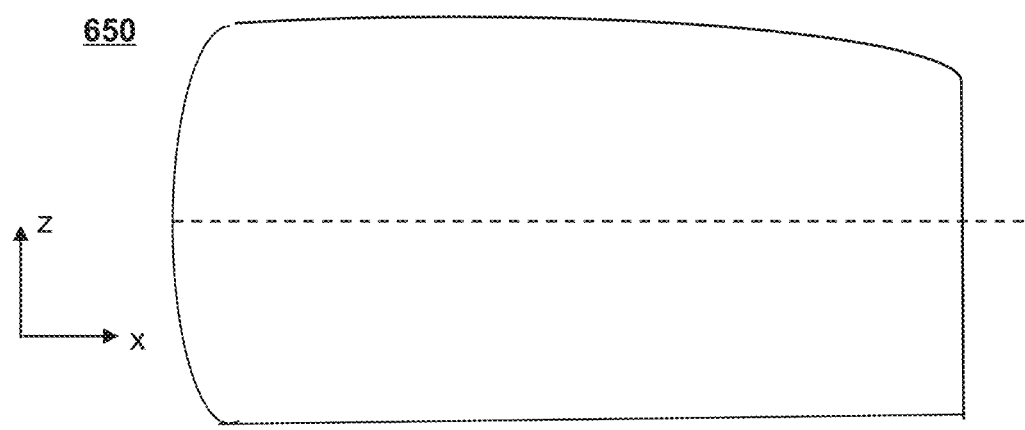
Figure 6F:
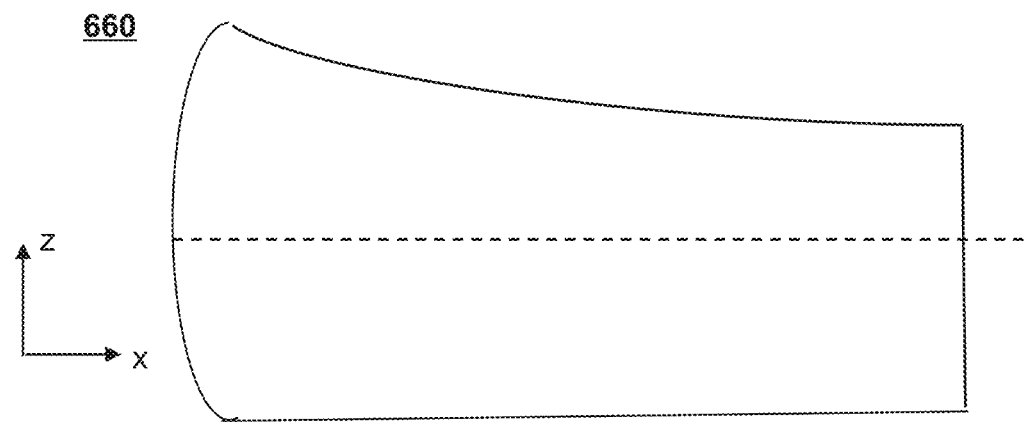

In some embodiments, the upper edge and the lower edge of the leaf 510 may be straight line(s). Merely by way of example, as shown in FIGS. 6A-6C, the upper edge and the lower edge of the leaf 610 (or leaf 620, or leaf 630) are straight lines. Thus, the thicknesses of the leaf 610 (or leaf 620, or leaf 630) may vary linearly along the longitudinal direction. Alternatively or additionally, the upper edge and/or the lower edge of the leaf 510 may not be straight line(s) (e.g., polylines, curved lines). For example, as shown in FIG. 6D, the upper edge of the leaf 640 is a polyline, and the lower edge of the leaf 640 is a straight line. Accordingly, the thicknesses of the leaf 640 may vary non-linearly along the longitudinal direction. As another example, as shown in FIGS. 6E and 6F, the upper edge of the leaf 650 (or leaf 660) is a curved line, and the lower edge of the leaf 650 (or leaf 660) is a straight line. Accordingly, the thicknesses of the leaf 650 (or leaf 660) may vary non-linearly along the longitudinal direction. Thus, the thicknesses of the leaf may vary linearly or non-linearly along the longitudinal direction (i.e., the x-direction).

Figure 6G:
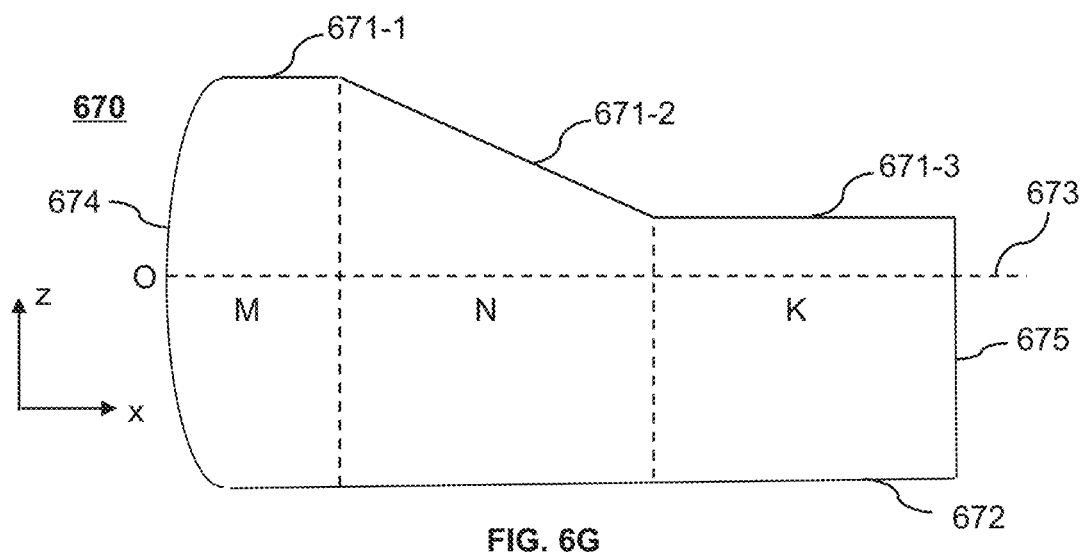

In some embodiments, only a portion of the leaf 510 may have thicknesses varying along the longitudinal direction of the leaf 510. For illustration purposes, FIG. 6G illustrates an exemplary leaf 670. As shown in FIG. 6G, the upper edge 671 of the leaf 670 is divided into three segments, i.e., a first segment 671-1, a second segment 671-2, and a third segment 671-3; and the leaf 670 is divided into three portions (i.e., a first portion M, a second portion N, and a third portion K). In the first portion M, the lower edge 672 and the first segment 671-1 of the upper edge 671 of the leaf 670 are parallel to the longitudinal direction of the leaf 670 (i.e., the x-direction). In the second portion N, the lower edge 672 of the leaf 670 is parallel to the longitudinal direction of the leaf 670, and the second segment 671-2 of the upper edge 671 is unparallel to the longitudinal direction of the leaf 670. Specifically, distances between locations (or points) on the second segment 671-2 and a center axis 673 of the leaf 670 may gradually decrease from the front end 674 to the rear end 675. The thicknesses of the second portion N of the leaf 670 may gradually decrease along the longitudinal direction of the leaf 670 (i.e., the x-direction). In the third portion K, the lower edge 672 and the first segment 671-1 of the upper edge 671 of the leaf 670 are parallel to the longitudinal direction of the leaf 670 (i.e., the x-direction).

Figure 6H:
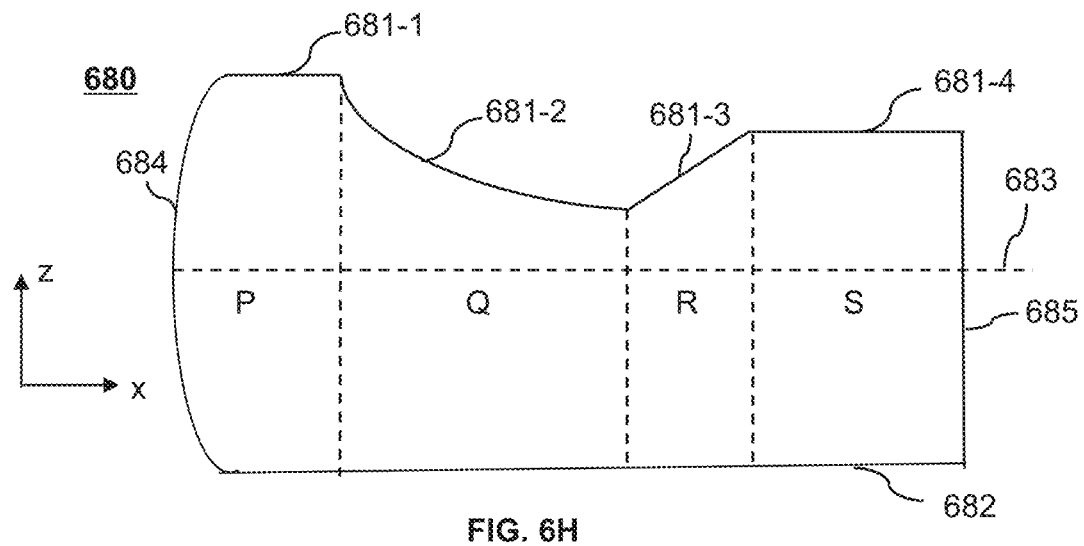

In some embodiments, the thicknesses of at least one portion of the leaf may vary non-monotonically along the longitudinal direction (i.e., the x-direction). For illustration purposes, FIG. 6H illustrates an exemplary leaf 680. As shown in FIG. 6H, the upper edge 681 of the leaf 680 is divided into four segments, i.e., a first segment 681-1, a second segment 681-2, a third segment 681-3, and a fourth segment 681-4; and the leaf 680 is divided into four portions (i.e., a first portion P, a second portion Q, a third portion R, and a fourth portion S). In the first portion P, the lower edge 682 and the first segment 681-1 of the upper dege 681 of the leaf 680 are parallel to the longitudinal direction of the leaf 680 (i.e., the x-direction). In the second portion Q, the lower edge 682 of the leaf 680 is parallel to the longitudinal direction of the leaf 680, and the second segment 681-2 of the upper edge 681 is unparallel to the longitudinal direction of the leaf 680. Specifically, distances between locations (or points) on the second segment 681-2 and a center axis 683 of the leaf 680 may gradually decrease from the front end 684 to the rear end 685. The thicknesses of the second portion N of the leaf 680 may gradually decrease along the longitudinal direction of the leaf 680 (i.e., the x-direction). In the third portion R, the lower edge 682 of the leaf 680 is parallel to the longitudinal direction of the leaf 680, and the third segment 681-3 of the upper edge 681 is unparallel to the longitudinal direction of the leaf 680. Specifically, distances between locations (or points) on the third segment 681-3 and a center axis 683 of the leaf 680 may gradually decrease from the front end 684 to the rear end 685. The thicknesses of the third portion R of the leaf 680 may gradually increase along the longitudinal direction of the leaf 680 (i.e., the x-direction). In the fourth portion S, the lower edge 682 and the fourth segment 681-4 of the upper dege 681 of the leaf 680 are parallel to the longitudinal direction of the leaf 680 (i.e., the x-direction).

Figure 6I:
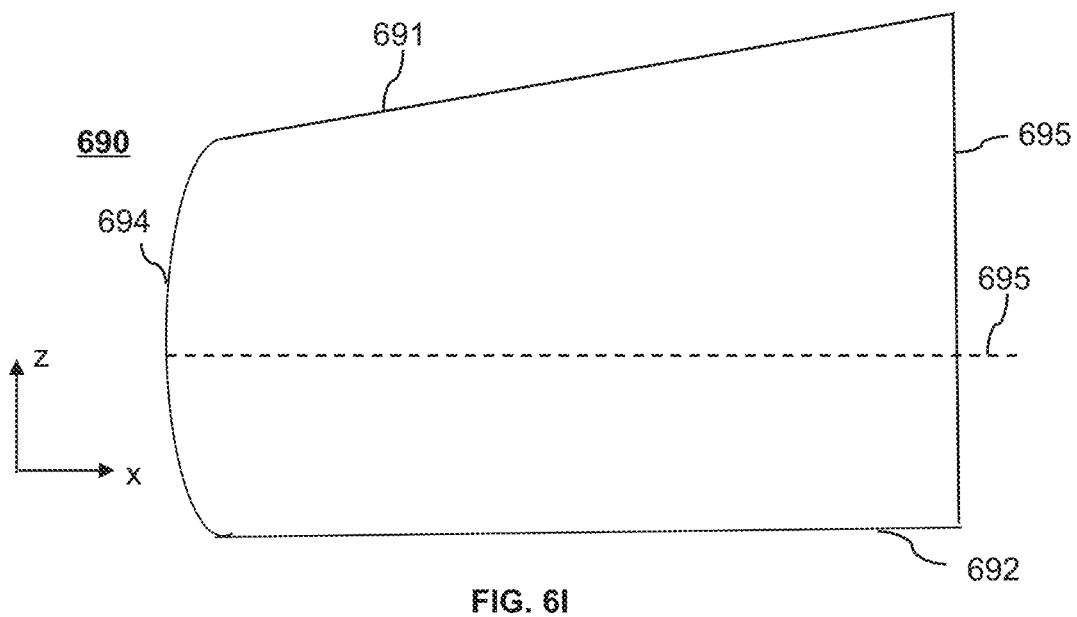

In some embodiments, the thicknesses of the leaf may gradually increase along the longitudinal direction of the leaf (i.e., the x-direction) from the front end to the rear end. For illustration purposes, FIG. 6I illustrates an exemplary leaf 690. As shown in FIG. 6I, the lower edge 692 of the leaf 690 is parallel to the longitudinal direction of the leaf 690, and the upper edge 691 of the leaf 690 is unparallel to the longitudinal direction of the leaf 690. Specifically, distances between locations (or points) on the upper edge 691 of the leaf 690 and a center axis 693 of the leaf 690 may gradually increase from the front end 694 to the rear end 695 of the leaf 690.

It should be noted that the leaves shown in FIGS. 6A-6I are merely examples and are not intended to limit the scope of the present disclosure. In some embodiments, the upper edge and/or the lower edge of the at least one portion of the leaf 510 may be a straight line, a polyline, a curved line, etc. For example, two edges of the leaf 510 may both be polylines such that the thicknesses of the leaf vary non-linearly. The polylines may be symmetric or asymmetric with respect to a center axis of the leaf 510. As another example, two edges of the leaf 510 may both be curved lines such that the thicknesses of the leaf vary non-linearly. The curved lines may be symmetric or asymmetric with respect to a center axis of the leaf 510. As a further example, one edge of the leaf 510 may be a polyline and the other edge of the leaf 510 may be a curved line. Thus, the leaf 510 may have any shape as long as different locations of the at least one portion of the leaf 510 have different thicknesses along the longitudinal direction within the leaf 510. It should also be noted that different leaves in the MLC may have different shapes. For example, the shape of at least some of the leaves 510 may be the same as or similar to the shape of the leaf 610 shown in FIG. 6A, and the shape of the other leaves 510 may be the same as or similar to the shape of the leaf 620 shown in FIG. 6B.

In radiotherapy, in order to achieve that the radiation source (e.g., the first radiation source 114) delivers a correctly shaped dose, the leaves need to be accurately positioned (e.g., the front end of each leaf needs to be accurately positioned). In some embodiments of the present disclosure, the thicknesses of the at least one portion of the leaf may vary along the longitudinal direction (i.e., the x-direction) of the leaf. Thus, the position of the leaf may be determined based on the thicknesses of two or more locations of the leaf, in which the thicknesses of the two or more locations of the leaf are different.

In some embodiments, a length-height correspondence of the leaf 510 may be determined based on factors including, e.g., the structure (e.g., shape and size) of the leaf 510, and/or an installation position of the MLC 500. For a location (or point) on the lower edge or the upper edge within the leaf 510, the length may refer to a distance between the location (or point) and the front end of the leaf 510 (or the rear end of the leaf 510) along the longitudinal direction (i.e. the x-direction) of the leaf. In some embodiments, the height may refer to a thickness of the leaf 510 at the location (or point). Alternatively, the height may refer to a distance between the location (or point) and a reference plane (e.g, a plane in which a measurement device is located). In some embodiments, the length-height correspondence of the leaf 510 may be determined based on thicknesses of the leaf 510 at multiple locations (or points) within the at least one portion of the leaf 510 where the thicknesses of the leaf 510 vary. Alternatively, the length-height correspondence of the leaf 510 may be determined based on distances between multiple locations (or points) on the lower edge or the upper edge within the at least one portion of the leaf 510 and the reference plane where the thicknesses of the leaf 510 vary. The length-height correspondence may be a mapping relationship or a function between height and length of the leaf 510. In some embodiments, the length-height correspondence may be a linear relationship or a non-linear relationship. The length-height correspondence may include a series of continuous values (e.g., a function) or a series of discrete values (length-height pairs).

In some embodiments, the MLC 500 may further include a measurement device (not shown in FIG. 5) mounted to a fixed position of the radiation system 100. For example, the measurement device may be mounted to the first radiation source 114. In this case, the measurement device may be used to determine an absolute position of a leaf 510. As another example, the measurement device may be mounted on a carriage of the MLC 500. In this case, the measurement device may be used to determine a relative position of a leaf 510. For instance, a relative position of a leaf 510 may be represented by a movement of a leaf 520 relative to a component of the radiation system 100 (e.g., the first radiation source 114). In some embodiments, the measurement device may be mounted at a position out of a radiation path of the first radiation source 114, which may help extend its service life. The measurement device may be configured to determine the height of a leaf 510 at a specific location of the leaf 510. In some embodiments, the height of a leaf at a specific location may refer to the thickness of the leaf at the specific location. Alternatively, the height of a leaf at a specific location may refer to a distance between the specific location on the lower edge or the upper edge of the leaf and a reference plane (e.g., a plane in which the measurement device is located, the center axis of the leaf 510). In some embodiments, the measurement device may include one or more measurement components configured to determine the height of each leaf 510 at the specific location in the longitudinal direction. A specific location may be a fixed location relative to the measurement component. For example, a line connecting a specific location and the measurement component may be parallel to the z-direction as illustrated in FIG. 7A In some embodiments, the measurement device may determine the height of a leaf using a light detection technique, etc.

Figure 7A:
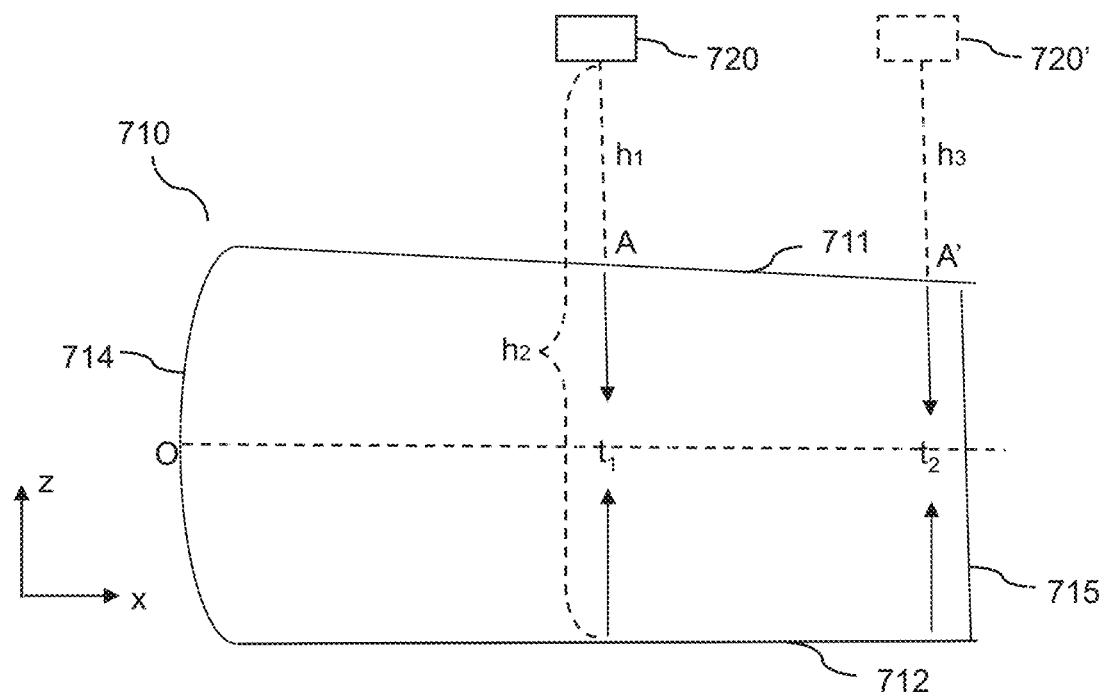
FIGS. 7A and 7B illustrate two exemplary approaches for determining a position of a leaf according to some embodiments of the present disclosure.

Merely by way of example, FIG. 7A illustrates an exemplary approach for determine a position of a leaf. As shown in FIG. 7A, the upper edge 711 of the leaf 710 is unparallel to the longitudinal direction of the leaf 710. The measurement device may include a measurement component 720 including a light source and a light detector (not shown in FIG. 7A). The upper edge 711 of the leaf 710 may be coated with a reflective film (e.g., ruby), which can reflect light. In some embodiments, the light source of the measurement component 720 may be positioned above the leaf 710 (as shown in FIG. 7A) and mounted to a fixed position of the radiation system 100. The specific location A of the leaf 710 may be a location on the leaf 710 that is irradiated by the light source. In some embodiments, light emitted by the light source may irradiate the leaf 710 vertically along the z-direction (as shown in FIG. 7A), and thus a line connecting the light source and the specific location A may be parallel to the z-direction. The light emitted by the light source may be reflected by the reflective film on the upper edge 711 of the leaf 710 and further be detected by the light detector. In some embodiments, the time that lapsed between light being emitted and being detected may be used to determine a first distance $h_1$ (a vertical distance along the z-direction) between the light source (or the measurement component) and the upper edge 711 of the leaf 710 at the specific location A. A second distance $h_2$ (a vertical distance along the z-direction) between the light source (or the measurement component) and the lower edge 612 of the leaf 610 may be known or measured. Thus, the thickness $t_1$ of the leaf 710 at the specific location A may be determined based on the first distance $h_1$ and the second distance $h_2$. In some embodiments, if the length-height correspondence of the leaf 710 relates to the thickness of the leaf 710 at a location (or point) within the at least one portion of the leaf 710, the height of the leaf 710 at the specific location A may be the thickness $t_1$ of the leaf 710 at the specific location A. Thus, a target distance between the first end (e.g., the front end 714) or the second end (e.g., the rear end 715) and the specific location A may be determined based on the thickness $t_1$ of the leaf 710 at the specific location A and the length-height correspondence of the leaf 710. Then, the position of the first end (e.g., the front end 714) or the second end (e.g., the rear end 715) may be determined based on the specific location A and the target distance. Alternatively, if the length-height correspondence of the leaf 710 relates to a distance between a location (or point) within the at least one portion of the leaf 710 and the reference plane, the height of the leaf 710 at the specific location A may be the first distance $h_1$ between the light source and the upper edge 711 of the leaf 710 at the the specific location A. Thus, a target distance between the first end (e.g., the front end 714) or the second end (e.g., the rear end 715) and the specific location A may be determined based on the first distance $h_1$ and the length-height correspondence of the leaf 710. Then, the position of the first end (e.g., the front end 714) or the second end (e.g., the rear end 715) may be determined based on the specific location A and the target distance. It should be noted that in some embodiments, light emitted by the light source may irradiate the leaf 710 obliquely, e.g., at an angle to the z-direction (not shown in FIG. 7A). The light emitted by the light source may be reflected by the reflective film on the upper edge 711 of the leaf 710 at a specific location and further be detected by the light detector. A line connecting the light source and the specific location may be unparallel to the z-direction. Since the light irradiates different positions of the leaf 710, the specific location may not be a fixed location relative to the light source (or the measurement component). A first distance $h_0$ between the light source and the upper edge 711 of the leaf 710 at the specific location may be determined based on the time that lapsed between light being emitted and being detected. Then a vertical distance $h'_z$ along the z-direction between the light source and the upper edge 711 of the leaf 710 at the specific location may be determined based on the first distance $h_0$. A horizontal distance $h'_x$ along the x-direction between the light source and the upper edge 711 of the leaf 710 at the specific location may also be determined based on the first distance $h_0$. The horizontal distance $h'_x$ may vary when the light irradiates different positions of the leaf 710. The second distance $h_2$ (a vertical distance along the z-direction) between the light source (or the measurement component) and the lower edge 612 of the leaf 610 may be known or measured. Thus, the thickness $t_0$ of the leaf 710 at the specific location may be determined based on the vertical distance $h'_z$ and the second distance $h_2$. A target distance between the first end (e.g., the front end 714) or the second end (e.g., the rear end 715) and the specific location may be determined based on the thickness to of the leaf 710 and the length-height correspondence of the leaf 710. Then the position of the first end (e.g., the front end 714) or the second end (e.g., the rear end 715) may be determined based on the position of the light source, the horizontal distance $h'_x$, and the target distance.

Figure 7B:
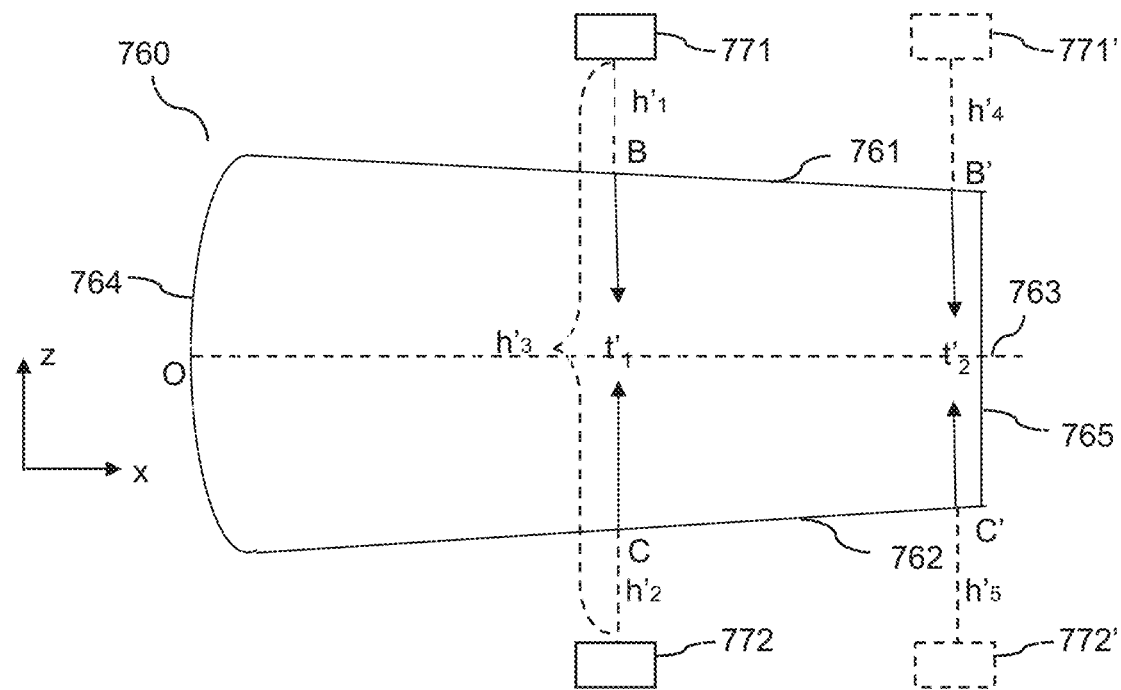

As another example, FIG. 7B illustrates another exemplary approach for determining a position of a leaf. As shown in FIG. 78, the upper and lower edges of the leaf 760 are unparallel to the longitudinal direction of the leaf 760. The measurement device may include two measurement components 771 and 772 each of which includes a light source and a light detector (not shown in FIG. 7). The upper edge 761 and the lower edge 762 of the leaf 760 may be coated with reflective films (e.g., ruby), which can reflect light. In some embodiments, a first light source of the measurement component 771 may be positioned above the leaf 760 (as shown in FIG. 78) and mounted to a fixed position of the radiation system 100. A second light source of the measurement component 772 may be positioned under the leaf 760 (as shown in FIG. 78) and mounted to a fixed position of the radiation system 100. In some embodiments, the first light source and the second light source may be symmetrical with respect to a center axis 763 of the leaf 760. The specific location B of the leaf 760 may be a location on the leaf 760 that is irradiated by the first light source. The specific location C of the leaf 760 may be a location on the leaf 760 that is irradiated by the second light source. In some embodiments, light emitted by the first and/or second light sources may irradiate the leaf 760 vertically along the z-direction. A line connecting the specific location B and the specific location C may be parallel to the z-direction. The light emitted by the first light source may be reflected by the reflective film on the upper edge 761 of the leaf 760 and further be detected by a first light detector. In some embodiments, the time that lapsed between light being emitted (by the first light source) and being detected (by the first light detector) may be used to determine a first distance $h'_1$ (a vertical distance along the z-direction) between the first light source (or the measurement component 771) and the upper edge 761 of the leaf 760 at the specific location B. The light emitted by the second light source may be reflected by the reflective film on the lower edge 762 of the leaf 760 and further be detected by a second light detector. In some embodiments, the time that lapsed between light being emitted (by the second light source) and being detected (by the second light detector) may be used to determine a second distance $h'_2$ (a vertical distance along the z-direction) between the second light source (or the measurement component 772) and the lower edge 762 at the specific location C. A third distance $h'_3$ between the first light source and the second light source may be known or measured. Then, the thickness $t'_1$ of the leaf 760 at the specific location B (or C) may be determined based on the first distance $h'_1$, the second distance $h'_2$, and the third distance $h'_3$. In some embodiments, if the length-height correspondence of the leaf 760 relates to the thickness of the leaf 760 at a location (or point) within the at least one portion of the leaf 760, the height of the leaf 760 at the specific location B (or C) may be the thickness $t'_1$ of the leaf 760 at the specific location B (or C). Thus, a target distance between the first end (e.g., the front end 764) or the second end (e.g., the rear end 765) and the specific location B (or C) may be determined based on the thickness $t'_1$ of the leaf 760 at the specific location B (or C) and the length-height correspondence of the leaf 760. Then, the position of the first end (e.g., the front end 764) or the second end (e.g., the rear end 765) of the leaf 760 may be determined based on the target distance and the specific location B (or C). Alternatively, if the length-height correspondence of the leaf 760 relates to a distance between a location (or point) within the at least one portion of the leaf 760 and the reference plane, the height of the leaf 760 at the specific location B (or C) may be the first distance $h'_1$ between the light source and the upper edge 761 of the leaf 760 at the the specific location B (or C), or the second distance $h'_2$ between the light source and the lower edge 762 of the leaf 760 at the the specific location B (or C). Thus, a target distance between the first end (e.g., the front end 764) or the second end (e.g., the rear end 765) and the specific location B (or C) may be determined based on the first distance $h'_1$ (or the second distance $h'_2$) and the length-height correspondence of the leaf 760. Thus, the position of the first end (e.g., the front end 764) or the second end (e.g., the rear end 765) of the leaf 760 may be determined based on the target distance and the specific location B (or C). It should be noted that in some embodiments, light emitted by the first light source and/or the second light source may irradiate the leaf 760 obliquely, e.g., at an angle to the z-direction (not shown in FIG. 7B). The first light source and the second light source may irradiate the leaf 760 symmetrically or asymmetrically. The light emitted by the first light source (or the second light source) may be reflected by the reflective film on the upper edge 761 (or the lower edge 762) of the leaf 760 at a specific location and further be detected by the first light detector (or the second light detector). A line connecting the first light source (or the second light source) and the specific location may be unparallel to the z-direction. The determination of the position of the first end (e.g., the front end 764) or the second end (e.g., the rear end 765) of the leaf 760 may be determined in a similar manner as the determination of the position of the first end (e.g., the front end 714) or the second end (e.g., the rear end 715) as described in FIG. 7A, and the descriptions thereof are not repeated. In some embodiments, the measurement device may include only one measurement component (the measurement component 771 or the measurement component 772) configured to determine the first distance $h'_1$ or the second distance $h'_2$. It should be noted that the above descriptions of the light detection technique are merely for illustration purposes, and are not intended to limit the scope of the present disclosure. In some embodiments, the height of the leaf 510 at the specific location may be determined according to other techniques.

In some embodiments, the MLC 500 may include a first measurement device and a second measurement device. The first measurement device may be configured to determine a first height of the leaf 510 at a first specific location in the longitudinal direction and the second measurement device may be configured to determine a second height of the leaf 510 at a second specific location in the longitudinal direction. The first height of the leaf 510 at the first specific location and the second height of the leaf 510 at the second specific location may be used to determine the position of the first end or the second end of the leaf 510. For example, as shown in FIG. 7A, a first height (e.g., the first distance $h_1$, or the thickness $t_1$) of the leaf 710 at the first specific location A may be determined by the first measurement device (the measurement component 720). A second height (e.g., a distance $h_3$, or a thickness $t_2$) of the leaf 710 at the second specific location A' may be determined by the second measurement device (a measurement component 720'). A position of the first end (e.g., the front end 714) or the second end (e.g., the rear end 715) of the leaf 710 may be determined based on the first height (e.g., the first distance $h_1$, or the thickness $t_1$) of the leaf 710 at the first specific location A and the second height (e.g., the distance $h_3$, or the thickness $t_2$) of the leaf 710 at the second specific location A' and the length-height correspondence of the leaf 610. Details regarding the determination of the position of the first end or the second end of the leaf 710 may be found elsewhere in the present disclosure (e.g, FIG. 10 and the descriptions thereof). As another example, as shown in FIG. 7B, a first height (e.g., the first distance $h'_1$, the second distance $h'_2$, or the thickness $t'_1$) of the leaf 760 at the first specific location B (or C) may be determined by the first measurement device (the measurement components 771 and 772). A second height (e.g., a distance $h'_4$, a distance $h'_5$, or a thickness $t'_2$) of the leaf 760 at the second specific location B' (or C') may be determined by a second measurement device (measurement components 771' and 772'). A position of the first end (e.g., the front end 764) or the second end (e.g., the rear end 765) of the leaf 760 may be determined based on the first height (e.g., the first distance $h'_1$, the second distance $h'_2$, or the thickness $t'_1$) of the leaf 760 at the first specific location B (or C) and the second height (e.g., the distance $h'_4$, the distance $h'_5$, or the thickness $t'_2$) of the leaf 760 at the second specific location B' (or C') and the length-height correspondence of the leaf 760. More descriptions of the determination of the position of the first end or the second end of the leaf 760 may be found elsewhere in the present disclosure (e.g., FIG. 10 and the descriptions thereof).

It should be noted that the above descriptions of the MLC 500 are merely provided for illustration purposes, and not intended to limit the scope of the present disclosure. For persons having ordinary skill in the art, multiple variations and modifications may be made under the teachings of the present disclosure. However, those variations and modifications do not depart from the scope of the present disclosure. In some embodiments, the measurement device may include a plurality of measurement components, each of which may correspond to a leaf 510 of the MLC 500 and may be configured to determine a height of the leaf 510 at the specific location in the longitudinal direction.

Figure 8:
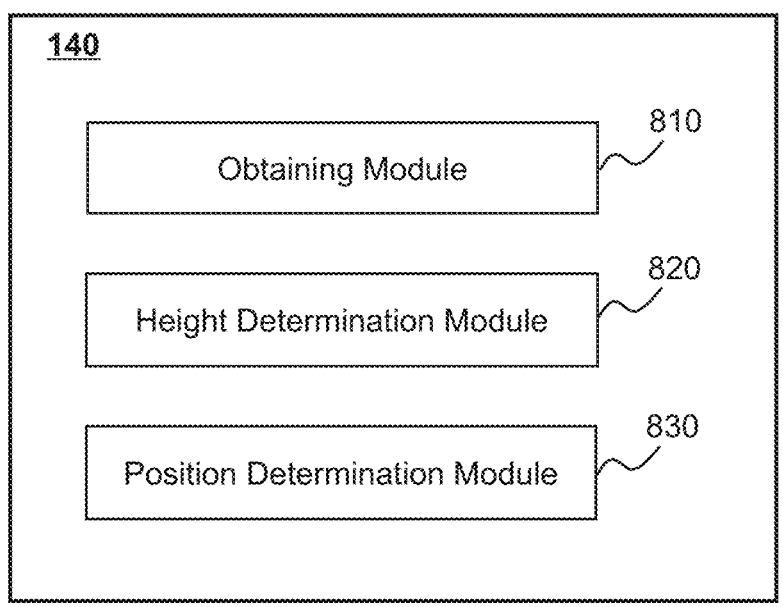
FIG. 8 is a block diagram illustrating an exemplary processing device according to some embodiments of the present disclosure.

FIG. 8 is a block diagram illustrating an exemplary processing device 140 according to some embodiments of the present disclosure. The processing device 140 may be implemented on the computing device 200 (e.g., the processor 210) as illustrated in FIG. 2 or the CPU 340 as illustrated in FIG. 3. The processing device 140 may include an obtaining module 810, a height determination module 820, and a position determination module 830.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof.

The obtaining module 810 may be configured to obtain information related to an MLC. The information may include the number of leaves, the structure (e.g., shape, size) of the leaves, a length-height correspondence of each leaf, or the like. In some embodiments, the obtaining module 810 may obtain a length-height correspondence of a leaf of the MLC. The leaf may have thicknesses varying along a longitudinal direction of the leaf (e.g., the x-direction shown in FIG. 4A). The leaf may have a first end and a second end along the longitudinal direction of the leaf. In some embodiments, the obtaining module 810 may obtain the length-height correspondence of the leaf from one or more components of the radiation system 100 (e.g., the terminal 130, the storage device 150, etc.).

The height determination module 820 may be configured to determine a height of the leaf of the MLC at a specific location using a measurement device. In some embodiments, the measurement device may be mounted to a fixed position of the radiation system 100, e.g., a position out of a radiation path of the first radiation source 114. The specific location may be a fixed location relative to the measurement device. For example, a specific location (e.g., the specific location A as illustrated in FIG. 7A) may refer to a location (or point) on the leaf that is irradiated by the measurement device. In some embodiments, a line connecting the specific location and the measurement device may be parallel to the z-direction as illustrated in FIG. 7A. In some embodiments, the measurement device may include a plurality of measurement components, each of which may correspond to a leaf of the MLC and may be configured to determine a height of the leaf at the specific location in the longitudinal direction. Alternatively, the measurement device may include one or more measurement components, each of which may correspond to two or more leaves of the MLC and may be configured to determine a height of the two or more leaves at the specific location in the longitudinal direction. In some embodiments, the height determination module 820 may simultaneously determine the height of each leaf of the MLC at the specific location. Alternatively, the height determination module 820 may determine the height of each leaf of the MLC at the specific location in sequence.

The position determination module 830 may be configured to determine a position of the first end of the leaf based on the height of the leaf at the specific location and the length-height correspondence of the leaf. The length-height correspondence may be a mapping relationship or a function between height and length of the leaf. A distance between the first end and the specific location may be determined based on the height of the leaf at the specific location and the length-height correspondence of the leaf. Then the position of the first end of the leaf may be determined based on the specific location and the distance.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 140 may include one or more additional modules. For example, the processing device 140 may include a storage module (not shown). The storage module may be configured to store data generated during any process performed by any component of the processing device 140.

Figure 9:
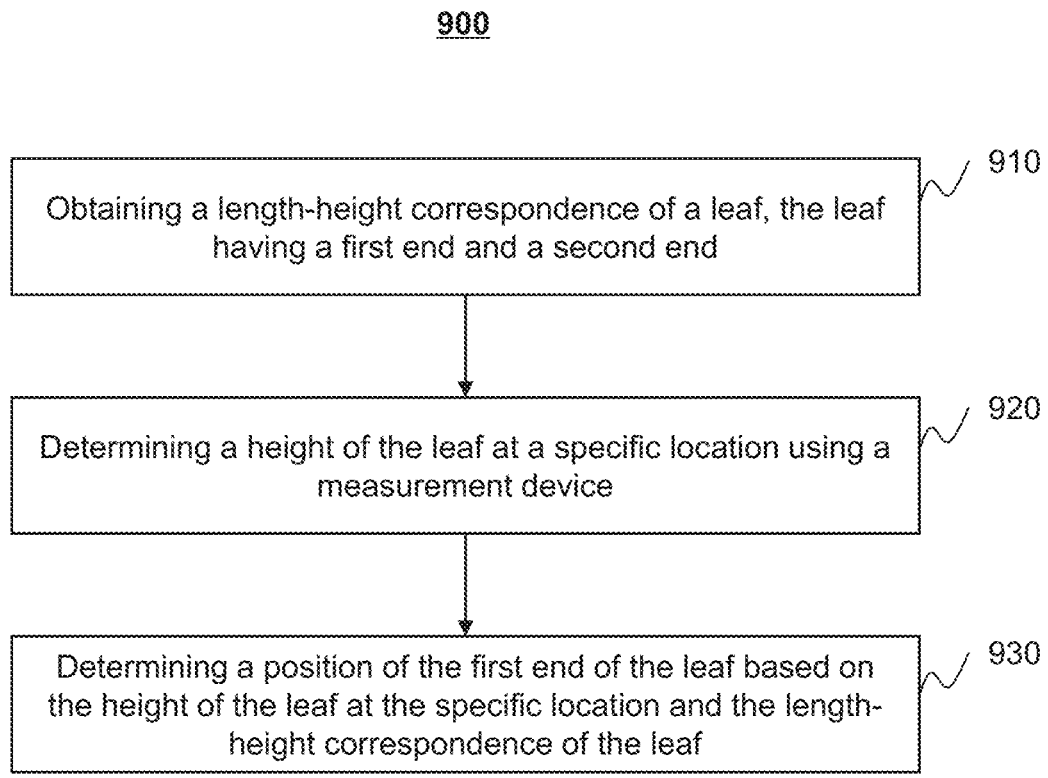
FIG. 9 is a flowchart illustrating an exemplary process for determining a position of a first end of a leaf of an MLC according to some embodiments of the present disclosure.

In some embodiments, for a treatment region, at least some of a plurality of leaves of an MLC (e.g., the MLC 500) may be moved to a desired position to define a desired aperture (e.g., radiation field). To implement the precise delivery of radiation to the treatment region, the position of each leaf should be accurately determined. In some embodiments, the position of an end (e.g., a front end) of each leaf may be used to represent the position of the corresponding leaf. FIG. 9 is a flowchart illustrating an exemplary process 900 for determining a position of a first end of a leaf of an MLC according to some embodiments of the present disclosure. The process 900 may be implemented in the radiation system 100 illustrated in FIG. 1. For example, the process 900 may be stored in the storage device 150 and/or the storage 220 in the form of instructions (e.g., an application), and invoked and/or executed by the processing device 140 (e.g., the processor 210 illustrated in FIG. 2, the CPU 340 as illustrated in FIG. 3, or one or more modules in the processing device 140 illustrated in FIG. 8). The operations of the illustrated process presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting.

In 910, the processing device 140 (e.g., the obtaining module 810) may obtain a length-height correspondence of a leaf. At least one portion of the leaf may have thicknesses varying along a longitudinal direction of the leaf (e.g., the x-direction shown in FIG. 4A). The leaf may have a first end and a second end along the longitudinal direction of the leaf. For example, the first end may refer to a front end of the leaf (e.g., the front end 412*a* shown in FIG. 4A) and the second end may refer to a rear end of the leaf (e.g., the rear end 412*b* shown in FIG. 4A). A lower edge and/or an upper edge of the at least one portion of the leaf may not be parallel to the longitudinal direction of the leaf such that different locations of the at least one portion of the leaf have different thicknesses along the longitudinal direction. The thicknesses of the at least one portion of the leaf may vary linearly or non-linearly along the longitudinal direction of the leaf. More descriptions regarding the structure (e.g., shape) of the leaf may be found elsewhere in the present disclosure (e.g., FIG. 5 and FIGS. 6A-6I, and the relevant descriptions thereof).

In some embodiments, the length-height correspondence of the leaf may be determined based on the structure (e.g., the shape and size) of the leaf, and/or an installation position of the leaf. For a location (or point) on the lower edge or the upper edge within the leaf, the length may refer to a distance between the location (or point) and the front end of the leaf (or the rear end of the leaf) along the longitudinal direction (i.e., the x-direction) of the leaf. In some embodiments, the height may refer to a thickness of the leaf at the location (or point). Alternatively, the height may refer to a distance between the location (or point) and a reference plane (e.g., a plane in which a measurement device is located). In some embodiments, the length-height correspondence of the leaf may be determined based on thicknesses of the leaf at multiple locations (or points) within the at least one portion of the leaf where the thicknesses of the leaf vary. Alternatively, the length-height correspondence of the leaf may be determined based on distances between multiple locations (or points) on the lower edge or the upper edge within the at least one portion of the leaf and the reference plane where the thicknesses of the leaf vary. The length-height correspondence of the leaf may be stored in a storage device (e.g., the storage device 150). The processing device 140 may obtain the length-height correspondence of the leaf from the storage device (e.g., the storage device 150).

In 920, the processing device 140 (e.g., the height determination module 820) may determine a height of the leaf at a specific location using a measurement device. In some embodiments, the measurement device may be mounted to a fixed position of the radiation system 100, e.g., a position out of a radiation path of the first radiation source 114. The specific location may be a fixed location relative to the measurement device. For example, a specific location may refer to a location on the leaf that is irradiated by the measurement device (e.g., the specific location A as illustrated in FIG. 7A). In some embodiments, a line connecting a specific location and the measurement device may be parallel to the z-direction as illustrated in FIG. 7A. In some embodiments, the height of the leaf at the specific location may be determined according to a light detection technique, etc. Details regarding the determination of the height of the leaf at the specific location may be found elsewhere in the present disclosure (e.g., FIGS. 7A and 7B, and the descriptions thereof).

In 930, the processing device 140 (e.g., the position determination module 830) may determine a position of the first end of the leaf based on the height of the leaf at the specific location and the length-height correspondence of the leaf. The length-height correspondence may be a mapping relationship or a function between height and length of the leaf. A distance between the first end and the specific location may be determined based on the height of the leaf at the specific location and the length-height correspondence of the leaf. Then the position of the first end of the leaf may be determined based on the specific location and the distance. The position of the first end of the leaf may be used to represent the position of the leaf.

It should be noted that the above description of the process 900 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, in 930, the processing device 140 may determine a position of the second end of the leaf based on the height of the leaf at the specific location and the length-height correspondence of the leaf. The position of the second end may be used to represent the position of the leaf.

In some embodiments, in order to further improve the accuracy of the determined position of the leaf, the processing device 140 may apply two or more measurement devices to determine the position of the leaf. Details may be found in, e.g., FIG. 10 and the relevant descriptions thereof.

Figure 10:
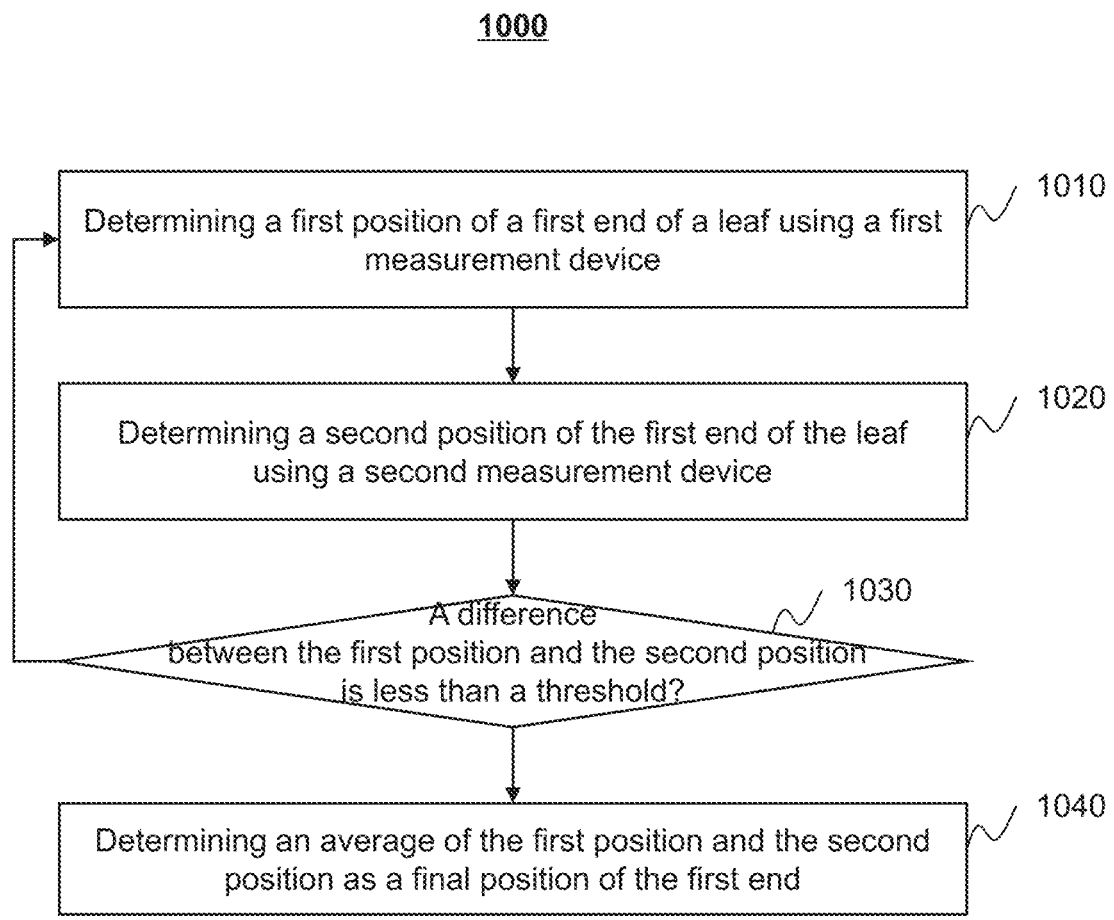
FIG. 10 is a flowchart illustrating an exemplary process for determining a position of a first end of a leaf of an MLC according to some embodiments of the present disclosure.

FIG. 10 is a flowchart illustrating an exemplary process 1000 for determining a position of a first end of a leaf of an MLC according to some embodiments of the present disclosure. The process 1000 may be implemented in the radiation system 100 illustrated in FIG. 1. For example, the process 1000 may be stored in the storage device 150 and/or the storage 220 in the form of instructions (e.g., an application), and invoked and/or executed by the processing device 140 (e.g., the processor 210 illustrated in FIG. 2, the CPU 340 as illustrated in FIG. 3, or one or more modules in the processing device 140 illustrated in FIG. 8). The operations of the illustrated process presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting.

In 1010, the processing device 140 (e.g., the position determination module 830) may determine a first position of a first end of a leaf using a first measurement device. In 1020, the processing device 140 (e.g., the position determination module 730) may determine a second position of the first end of the leaf using a second measurement device. In some embodiments, the first measurement device and the second measurement device may be mounted to different positions of the radiation system 100. The first measurement device may correspond to a first specific location of the leaf. The second measurement device may correspond to a second specific location of the leaf. In some embodiments, the processing device 140 may determine a first height of the leaf at the first specific location using the first measurement device. The processing device 140 may determine a first position of the first end of the leaf based on the first height of the leaf at the first specific location and a length-height correspondence of the leaf. The processing device 140 may determine a second height of the leaf at the second specific location using the second measurement device. The processing device 140 may determine a second position of the first end of the leaf based on the second height of the leaf at the second specific location and the length-height correspondence of the leaf. Details regarding the determination of the first (or second) position of the first end may be found elsewhere in the present disclosure (e.g., FIG. 9 and the descriptions thereof).

In 1030, the processing device 140 (e.g., the position determination module 830) may determine whether a difference between the first position and the second position is less than a threshold. In some embodiments, the threshold may be a default value or an empirical value related to the radiation system 100. For example, the threshold may be set according to a default setting of the radiation system 100, or preset or adjusted by a user. In response to a determination that the difference between the first position and the second position is less than a threshold, the processing device 140 may proceed to operation 1040. In 1040, the processing device 140 (e.g., the position determination module 1030) may determine an average of the first position and the second position as a final position of the first end. Alternatively, in response to a determination that the difference between the first position and the second position exceeds the threshold, the processing device 140 may proceed to operation 1010. The processing device 140 (e.g., the position determination module 830) may re-determine the first position of the first end using the first measurement device and/or the second position of the first end using the second measurement device. The processing device 140 may repeat operations 1010 to 1030 until the difference between the first position and the second position is less than the threshold. In some embodiments, if the difference between the first position and the second position exceed the threshold, the processing device 140 may send an instruction to the radiation delivery device 110 to stop delivering radiation to the subject. The MLC may be automatically inspected by the radiation delivery device 110 or manually inspected by a user or operator.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the users computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A multi-leaf collimator, comprising:
a plurality of leaves, at least two leaves of the plurality of leaves being movable parallel to each another along a longitudinal direction of each of the at least two leaves to define an aperture, wherein at least one portion of each leaf of at least some of the plurality of leaves has thicknesses varying along the longitudinal direction of each leaf; and
a measurement device fixedly mounted on a radiation system that employs the multi-leaf collimator, the measurement device being configured to determine a height of each leaf at a specific location in the longitudinal direction, wherein the specific location is a fixed location relative to the measurement device, and the height of each leaf at the specific location is used to determine a position of a first end that forms the aperture or a position of a second end of each leaf.

2. The multi-leaf collimator of claim 1, wherein
at least one of a lower edge or an upper edge of the at least one portion of each leaf is unparallel to the longitudinal direction such that different locations of the at least one portion of each leaf have different thicknesses along the longitudinal direction.

3. The multi-leaf collimator of claim 1, wherein
the thicknesses of the at least one portion of each leaf vary linearly along the longitudinal direction of each leaf.

4. The multi-leaf collimator of claim 1, wherein
the thicknesses of the at least one portion of each leaf vary non-linearly along the longitudinal direction of each leaf.

5. The multi-leaf collimator of claim 1, wherein
each leaf has a first end and a second end along the longitudinal direction of each leaf,
the first end of each leaf that forms the aperture has a maximum thickness within each leaf, and the second end of each leaf has a minimum thickness within each leaf.

6. The multi-leaf collimator of claim 1, wherein the height of each leaf at the specific location refers to the thickness of each leaf at the specific location.

7. The multi-leaf collimator of claim 1, wherein the height of each leaf at the specific location relates to a distance between the specific location on a lower edge or an upper edge of each leaf and a reference plane.

8. The multi-leaf collimator of claim 1, further comprising:
a second measurement device fixedly mounted on the radiation system and configured to determine a second height of each leaf at a second specific location in the longitudinal direction, wherein
the second specific location is a second fixed location relative to the second measurement device, and
the height of each leaf at the specific location and the second height of each leaf at the second specific location are used to determine the position of the first end or the position of the second end of each leaf.

9. The multi-leaf collimator of claim 1, wherein
the measurement device includes one or more measurement components configured to determine a height of each leaf at the specific location in the longitudinal direction.

10. The multi-leaf collimator of claim 1, wherein
the measurement device includes a plurality of measurement components, each of the plurality of measurement components being configured to determine a height of one of the at least some of the plurality of leaves at the specific location in the longitudinal direction.

11. A system, comprising:
at least one storage device including a set of instructions for determining a position of a leaf in a multi-leaf collimator, wherein the multi-leaf collimator includes a plurality of leaves, at least two leaves of the plurality of leaves being movable parallel to each another along a longitudinal direction of each of the at least two leaves to define an aperture;
at least one processor in communication with the at least one storage device, wherein when executing the set of instructions, the at least one processor is configured to cause the system to perform operations including:
obtaining a length-height correspondence of the leaf, wherein at least one portion of the leaf has thicknesses varying along the longitudinal direction of the leaf, the leaf having a first end and a second end along the longitudinal direction of the leaf;
determining a height of the leaf at a specific location using a measurement device, wherein the specific location is a fixed location relative to the measurement device; and
determining a position of the first end of the leaf that forms the aperture based on the height of the leaf at the specific location and the length-height correspondence of the leaf.

12. The system of claim 11, wherein the at least one processor is configured to cause the system to perform additional operations including:
determining a second height of the leaf at a second specific location using a second measurement device, wherein the second specific location is a second fixed location relative to the second measurement device; and
determining a second position of the first end of the leaf based on the second height of the leaf at the second specific location and the length-height correspondence of the leaf.

13. The system of claim 12, wherein the at least one processor is configured to cause the system to perform additional operations including:
determining a difference between the position and the second position of the first end of the leaf; and
in response to a determination that the difference between the position and the second position of the first end of the leaf is less than a threshold, determining an average of the position and the second position as a final position of the first end.

14. The system of claim 13, wherein the at least one processor is configured to cause the system to perform additional operations including:
in response to a determination that the difference between the position and the second position of the first end of the leaf exceeds the threshold, re-determining the position of the first end using the measurement device and/or the second position of the first end using the second measurement device.

15. The system of claim 11, wherein
at least one of a lower edge or an upper edge of the at least one portion of the leaf is unparallel to the longitudinal direction such that different locations of the at least one portion of the leaf have different thicknesses along the longitudinal direction.

16. The system of claim 15, wherein
the thicknesses of the at least one portion of the leaf vary linearly or non-linearly along the longitudinal direction of the leaf.

17. The system of claim 11, wherein the length-height correspondence of the leaf relates to the thickness of the leaf at a location within the at least one portion of the leaf.

18. The system of claim 11, wherein the length-height correspondence of the leaf relates to a distance between a location on the lower edge or the upper edge within the at least one portion of the leaf and a reference plane.

19. A method for determining a position of a leaf in a multi-leaf collimator implemented on a computing device having at least one processor, at least one computer-readable storage medium, and a communication platform connected to a network, the multi-leaf collimator including a plurality of leaves, at least two leaves of the plurality of leaves being movable parallel to each another along a longitudinal direction of each of the at least two leaves to define an aperture, comprising:
obtaining a length-height correspondence of the leaf, wherein at least one portion of the leaf has thicknesses varying along the longitudinal direction of the leaf, the leaf having a first end and a second end along the longitudinal direction of the leaf;
determining a height of the leaf at a specific location using a measurement device, wherein the specific location is a fixed location relative to the measurement device; and
determining a position of the first end of the leaf that forms the aperture based on the height of the leaf at the specific location and the length-height correspondence of the leaf.

* * * * *